US 8,455,427 B2

(12) United States Patent
Maines

(10) Patent No.: US 8,455,427 B2
(45) Date of Patent: Jun. 4, 2013

(54) METHODS OF MODIFYING INSULIN SIGNALING USING BILIVERDIN REDUCTASE

(75) Inventor: Mahin D. Maines, Rochester, NY (US)

(73) Assignee: University of Rochester, Rochester, NY (US)

(*) Notice: Subject to any disclaimer, the term of this patent is extended or adjusted under 35 U.S.C. 154(b) by 1026 days.

(21) Appl. No.: 11/816,557

(22) PCT Filed: Feb. 21, 2006

(86) PCT No.: PCT/US2006/005955
§ 371 (c)(1), (2), (4) Date: May 16, 2008

(87) PCT Pub. No.: WO2006/089270
PCT Pub. Date: Aug. 24, 2006

(65) Prior Publication Data
US 2009/0214627 A1    Aug. 27, 2009

Related U.S. Application Data

(60) Provisional application No. 60/654,394, filed on Feb. 18, 2005.

(51) Int. Cl.
A61K 38/04 (2006.01)
(52) U.S. Cl.
USPC .............................. 514/1.1; 530/300; 530/330
(58) Field of Classification Search
None
See application file for complete search history.

(56) References Cited

U.S. PATENT DOCUMENTS

| 2003/0027124 A1 | 2/2003 | Maines |
| 2005/0119205 A1 | 6/2005 | Maines |
| 2005/0287132 A1 | 12/2005 | Maines |
| 2007/0117769 A1 | 5/2007 | Maines |

OTHER PUBLICATIONS

Maines et al., Nuclear localization of biliverdin reductase in the rat kidney: response to nephrotoxins that induce heme oxygenase-1, J Pharmacol Exp Ther. 296(3):1091-7, 2001.*
Maines, New Insights into Biliverdin Reductase Functions: Linking Heme Metabolism to Cell Signaling, Physiology 20:382-389, 2005.*
Wu et al., Old biliverdin reductase: Links to insulin resistance and may be a novel therapeutic target, Med Hypotheses. 71(1):73-6, 2008.*
Kapitulnik et al. Pleiotropic functions of biliverdin reductase: cellular signaling and generation of cytoprotective and cytotoxic bilirubin, Trends Pharmacol Sci. 30(3):129-37, 2009.*
Almeida, Role of the haem oxygenase-carbon monoxide pathway in insulin-induced hypothermia: evidence for carbon monoxide involvement, Pflügers Arch—Eur J Physiol 444:244-250, 2002.*

(Continued)

Primary Examiner — Sharmila G. Landau
Assistant Examiner — Stephanie McNeil
(74) Attorney, Agent, or Firm — Riverside Law LLP

(57) ABSTRACT

The present invention relates to a method of modulating insulin signaling in a cell. This method involves modifying the nuclear or cellular concentration of biliverdin reductase, or fragments or variants thereof, in a cell, whereby a change in nuclear or cellular concentration of biliverdin reductase, or fragments or variants thereof, modulates insulin signaling in the cell via biliverdin reductase interaction with one or both of insulin receptor kinase domain and insulin receptor substrate. Also disclosed are methods of treating a condition associated with insulin signaling and treating a patient for a condition associated with insulin-mediated glucose uptake.

4 Claims, 7 Drawing Sheets

OTHER PUBLICATIONS

Khan et al. Impact of simvastatin on adipose tissue: pleiotropic effects in vivo, Endocrinology 150(12):5262-72, 2009.*

Zirbes et al., Cystic fibrosis related diabetes, Paediatr. Respir. Rev. 10(3):118-23, 2009.*

Proesmans et al., What's new in cystic fibrosis? From treating symptoms to correction of the basic defect. Eur J Pediatr. 167(8):839-49, 2008.*

Riordan, CFTR Function and Prospects for Therapy. Annu Rev Biochem. 77:701-26, 2008.*

Rich et al., Expression of cystic fibrosis transmembrane conductance regulator corrects defective chloride channel regulation in cystic fibrosis airway epithelial cells. Nature, 347(6291):358-63, 1990.*

Kaye et al., A single amino acid substitution results in a retinoblastoma protein defective in phosphorylation and oncoprotein binding, Proc. Natl. Acad. Sci. USA, vol. 87, pp. 6922-6926, 1990.*

Skolnick et al., From genes to protein structure and function: novel applications of computational approaches in the genomic era, Trends in Biotechnol. 18(1):34-39, 2000.*

Lerner-Marmarosh et al. "Human Biliverdin Reductase: A Member of the Insulin Receptor Substrate Family With Serine/Threonine/Tyrosine Kinase Activity," PNAS, 102(20): 7109-7114 (2005).

Maines, "New Insights Into Biliverdin Reductase Functions: Linking Heme Metabolism to Cell Signaling," 23: 382-389 (2005).

PCT Search Report for PCT/US06/05955.

European Search Report for corresponding EP application 06720910.6 (dated Apr. 7, 2009).

Maines et al., "Nuclear Localization of Biliverdin Reductase in the Rat Kidney: Response to Nephrotoxins that Induce Heme Oxygenase-1," J. Pharmacol. Exp. Therapeut. 296(3):1091-1097(2000).

Miralem et al., "Small Interference RNA-Mediated Gene Silencing of Human Biliverdin Reductase, but not that of Heme Oxygenase-1, Attenuates Arsenite-Mediated Induction of the Oxygenase and Increases Apoptosis in 293A Kidney Cells," J. Biol. Chem. 280(17):17084-17092 (2005).

Kim et al., "Caveolae Compartmentalization of Heme Oxygenase-1 in Endothelial Cells," FASEB J. 18:1080-1089 (2004).

* cited by examiner

```
CLUSTAL W (1.82) multiple sequence alignment

Human BVR    MNAEPERKFGVVVVGVGRAGSVRMRDLRNPHPSSAFLNLIGFVSRRELGSIDGVQQISLE 60
Pig BVR      MNAEPERKFGVVVVGVGRAGSVRMRDLRNPHPSSAFLNLIGFVSRRELGSIDGVQQISLE 60
Rat BVR      MDAEPKRKFGVVVVGVGRAGSVRLRDLKDPR-SAAFLNLIGFVSRRELGSLDEVRQISLE 59
Mouse BVR    MSTEPKRKFGVVVVGVGRAGSVRIRDSKDPH-SSAFLNLIGYVSRRELGSLDNVRQISLE 59
              *..*:**:*********:***::* ::*: *:*******:********.* *:*****

Human BVR    DALSSQEVEVAYICSESSSHEDYIRQFLNAGKHVLVEYPMTLSLAAAQELWELAEQKGKV 120
Pig BVR      DALSSQEVEVAYICSESSSHEDYIRQFLNAGKHVLVEYPMTLSLAAAQELWELAEQKGKV 120
Rat BVR      DALRSQEIDVAYICSESSSHEDYIRQFLQAGKHVLVEYPMTLSFAAAQELWELAAQKGRV 119
Mouse BVR    DALRSQEVDVAYICTESSSHEDYIRQFLQAGKHVLVEYPMALSFAAAQELWELAAQKGRV 119
Chimp BVR                                          MTLSLAAAQELWELAEQKGKV 21
             *** ***:.:****.*************:***********:**:********** ***:*

Human BVR    LHEEHVELLMEEFAFLKKEVVGKDLLKGSLLFTSDPLEEDRFGFPAFSGISRLTWLVSLF 180
Pig BVR      LHEEHVELLMEEFAFLKKEVVGKDLLKGSLLFTAGPLEEERFGSPAFSGISRLTWLVSLF 180
Rat BVR      LHEEHVELLMEEFEFLRREVLGKELLKGSLRFTASPLEEERFGFPAFSGISRLTWLVSLF 179
Mouse BVR    LHEEHIELLMEEFLKREVAGKELLKGSLRFTASPLEEEKFGFPAFSGISRLTWLVSLF 179
Chimp BVR    LHEEHVELLMEEFAFLKKEVVGKDLLKGSLLFTAGPLEEERFGFPAFSGISRLTWLVSLF 81
             *****:******* **::** **::****** **:.****::** ****************

Human BVR    GELSLVSATLEERKEDQYMKMTVCLETEKKSPLSWIEEKGPGLKRNRYLSFHFKSGSLEN 240
Pig BVR      GELSLVSATLEERKEDQYMKMTVCLETEKKSPLSWIEEKGPGLKRNRYLSFHFKSGSLEN 240
Rat BVR      GELSLISATLEERKEDQYMKMTVQLETQNKGLLSWIEEKGPGLKRNRYVNFQFTSGSLEE 239
Mouse BVR    GELSLISATMENRKEDQYMKMTVQLETQNKSPLSWIEEKGPGLKRNRHISIHFKSGSLEE 239
Chimp BVR    GELSLVSATLEERKEDQYMKMTVCLETEKKSPLSWIEEKGPGLKRNRYLSFHFKSGSLEN 141
             *****:***:*:***********. ***::*  ******************:::.:*.*****:

Human BVR    VPNVGVNKNIFLKDQNIFVQKLLGQFSEKELAAEKKRILHCLGLAEEIQKYCCSRK 296
Pig BVR      VPNVGVNKNIFLKDQNIFVQKLLGQFSEKELAAEKKRILHCLGLAEEIQKYCCSRK 296
Rat BVR      VPSVGVNKNIFLKDQDIFVQKLLDQVSAEDLAAEKKRIMHCLGLASDIQKLCHQKK 295
Mouse BVR    VPNVGVNKNIFLKDQDIFIQKLLGQVSAEDLAAEKKRILHCLELASDIQRLCHRKQ 295
Chimp BVR    VPNVGVNKNIFLKDQNIFVQKLLGQFSEKELAAEKKRILHCLGLAEEIQKYCCSRK 197
             **.************:**:****.*.*::**********:****.:**::**: *  ::
```

Figure 1

```
atgaatgcag agcccgagag gaagtttggc gtggtggtgg ttggtgttgg ccgagccggc  60
tccgtgcgga tgagggactt gcggaatcca caccttcct cagcgttcct gaacctgatt 120
ggcttcgtgt cgagaaggga gctcgggagc attgatggag tccagcagat ttctttggag 180
gatgctcttt ccagccaaga ggtggaggtc gcctatatct gcagtgagag ctccagccat 240
gaggactaca tcaggcagtt ccttaatgct ggcaagcacg tccttgtgga atacccatg  300
acactgtcat tggcggccgc tcaggaactg tgggagctgg ctgagcagaa aggaaaagtc 360
ttgcacgagg agcatgttga actcttgatg gaggaattcg ctttcctgaa aaagaagtg  420
gtggggaaag acctgctgaa agggtcgctc ctcttcacat ctgacccgtt ggaagaagac 480
cggtttggct tccctgcatt cagcggcatc tctcgactga cctggctggt ctccctcttt 540
ggggagcttt ctcttgtgtc tgccactttg gaagagcgaa aggaagatca gtatatgaaa 600
atgacagtgt gtctggagac agagaagaaa agtccactgt catggattga agaaaaagga 660
cctggtctaa aacgaaacag atatttaagc ttccatttca agtctggtc cttggagaat  720
gtgccaaatg taggagtgaa taagaacata tttctgaaag atcaaatat atttgtccag  780
aaactcttgg gccagttctc tgagaaggaa ctggctgctg aaaagaaacg catcctgcac 840
tgcctggggc ttgcagaaga aatccagaaa tattgctgtt caaggaagta a            891
```

Figure 2

```
atggatgccg agccaaagag gaaatttgga gtggtagtgg ttggtgttgg cagagctggc    60
tcggtgaggc tgagggactt gaaggatcca cgctctgcag cattcctgaa cctgattgga   120
tttgtgtcca gacgagagct tgggagcctt gatgaagtac ggcagatttc tttggaagat   180
gctctccgaa gccaagagat tgatgtcgcc tatatttgca gtgagagttc cagccatgaa   240
gactatatac ggcagtttct gcaggctggc aagcatgtcc tcgtggaata ccccatgaca   300
ctgtcatttg cggcggccca ggagctgtgg gagctggccg cacagaaagg gagagtcctg   360
catgaggagc acgtggaact cttgatggag gaattcgaat tcctgagaag agaagtgttg   420
gggaagagc tactgaaagg gtctcttcgc ttcacagcta gcccactgga agaagagaga   480
tttggcttcc ctgcgttcag cggcatttct cgcctgacct ggctggtctc cctcttcggg   540
gagctttctc ttatttctgc caccttggaa gagcgaaaag aggatcagta tatgaaaatg   600
accgtgcagc tggagaccca gaacaagggt ctgctgtcat ggattgaaga gaaagggcct   660
ggcttaaaaa gaaacagata tgtaaacttc cagttcactt ctgggtccct ggaggaagtg   720
ccaagtgtag gggtcaataa gaacattttc ctgaaagatc aggatatatt tgttcagaag   780
ctcttagacc aggtctctgc agaggacctg gctgctgaga agaagcgcat catgcattgc   840
ctggggctgg ccagcgacat ccagaagctt tgccaccaga gaagtga                 888
```

Figure 3

```
atgaatgcag agcccgagag gaagtttggc gtggtggtgg ttggtgttgg ccgagccggc    60
tccgtgcgga tgagggactt gcggaatcca cacccttcct cagcgttcct gaacctgatt   120
ggcttcgtgt cgagaaggga gctcgggagc attgatggag tccagcagat ttctttggag   180
gatgctcttt ccagccaaga ggtggaggtc gcctatatct gcagtgagag ctccagccat   240
gaggactaca tcaggcagtt ccttaatgct ggcaagcacg tccttgtgga ataccccatg   300
acactgtcat tggcggccgc tcaggaactg tgggagctgg ctgagcagaa aggaaaagtc   360
ttgcacgagg agcatgttga actcttgatg gaggaattcg ctttcctgaa aaaagaagtg   420
gtggggaaag acctgctgaa agggtcgctc ctcttcacag ctggcccgtt ggaagaagag   480
cggtttggct cccctgcatt cagcggcatc tctcgcctga cctggctggt ctccctcttt   540
ggggagcttt ctcttgtgtc tgccactttg gaagagcgaa aggaagatca gtatatgaaa   600
atgacagtgt gtctggagac agagaagaaa agtccactgt catggattga agaaaaagga   660
cctggtctaa acgaaacag atatttaagc ttccatttca gtctgggtc cttgagaat    720
gtgccaaacg taggagtgaa taagaacata tttctgaaag atcaaaatat atttgtccag   780
aaactcttgg gccagttctc tgagaaggaa ctgctgctg aaaagaaacg catcctgcac   840
tgcctgggc ttgcagaaga aatccagaaa tattgctgtt caaggaagta a             891
```

Figure 4

```
ttacttcctt gaacagcaat atttctggat tcttctgca agccccaggc agtgcaggat     60
gcgtttcttt tcagcagcca gttccttctc agagaactgg cccaagagtt tctggacaaa   120
tatattttga tctttcagaa atatgttctt attcactcct acatttggca cattctccaa   180
ggacccagac ttgaaatgga aacttaaata tctgtttcgt tttagaccag gtccttttc    240
ttcaatccat gacagtggac ttttcttctc tgtctccaga cacactgtca ttttcatata   300
ctgatcttcc tttcgctctt ccaaagtggc agacacaaga gaaagctccc aaagaggga   360
gaccagccag gtcaggcgag agatgccgct gaatgcaggg aagccaaacc gctcttcttc   420
caacgggcca gctgtgaaga ggagcgaccc tttcagcagg tctttcccca ccacttcttt   480
tttcaggaaa gcgaattcct ccatcaagag ttcaacatgc tcctcgtgca agactttttcc   540
tttctgctca gccagctccc acagttcctg agcggccgcc aatgacagtg tcat         594
```

Figure 5

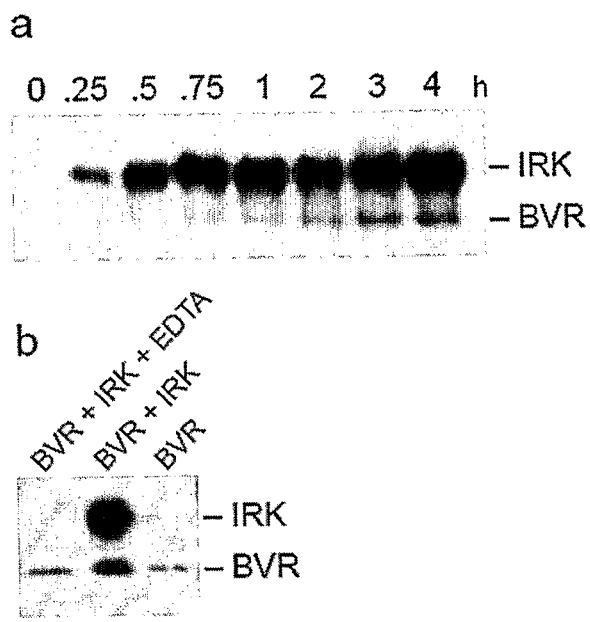
Figures 7A-B
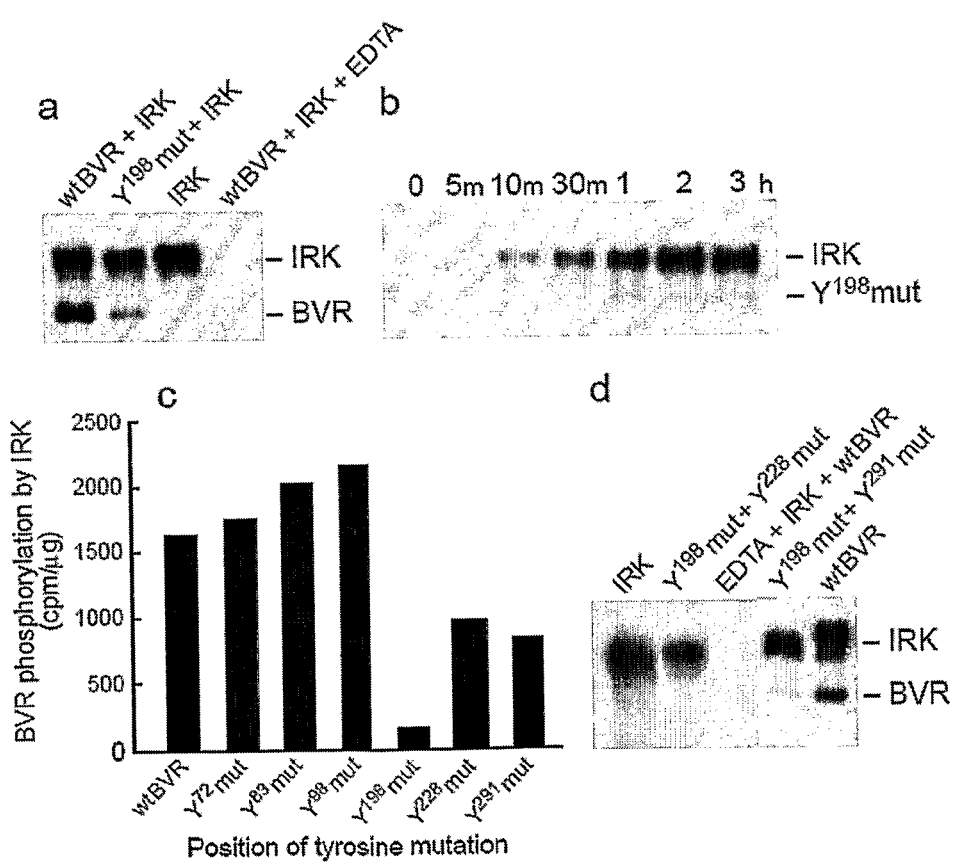
Figures 8A-D

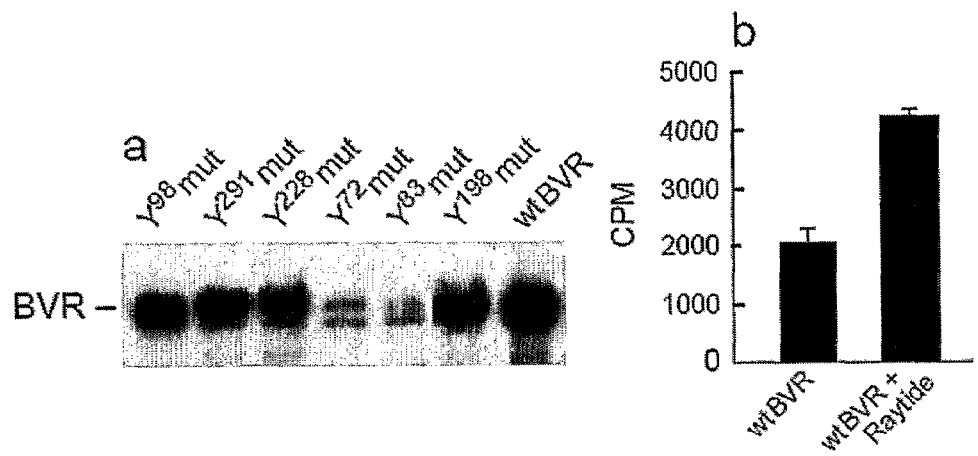
Figures 9A-B
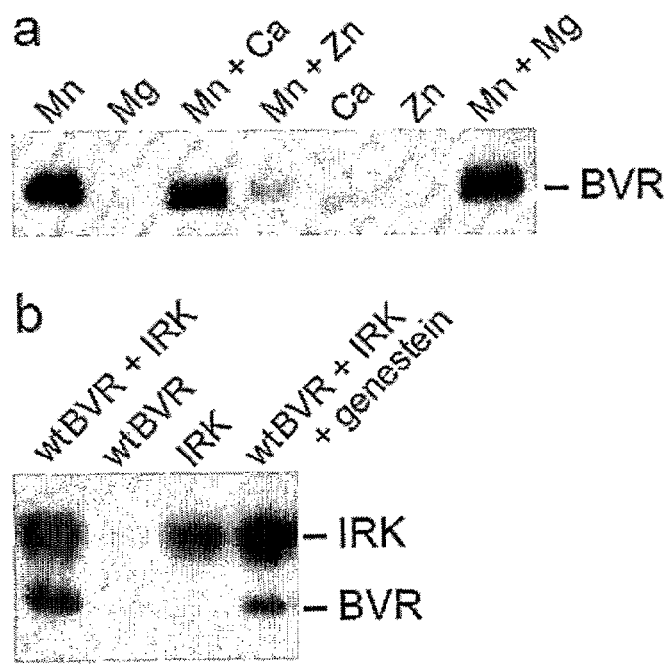
Figures 10A-B

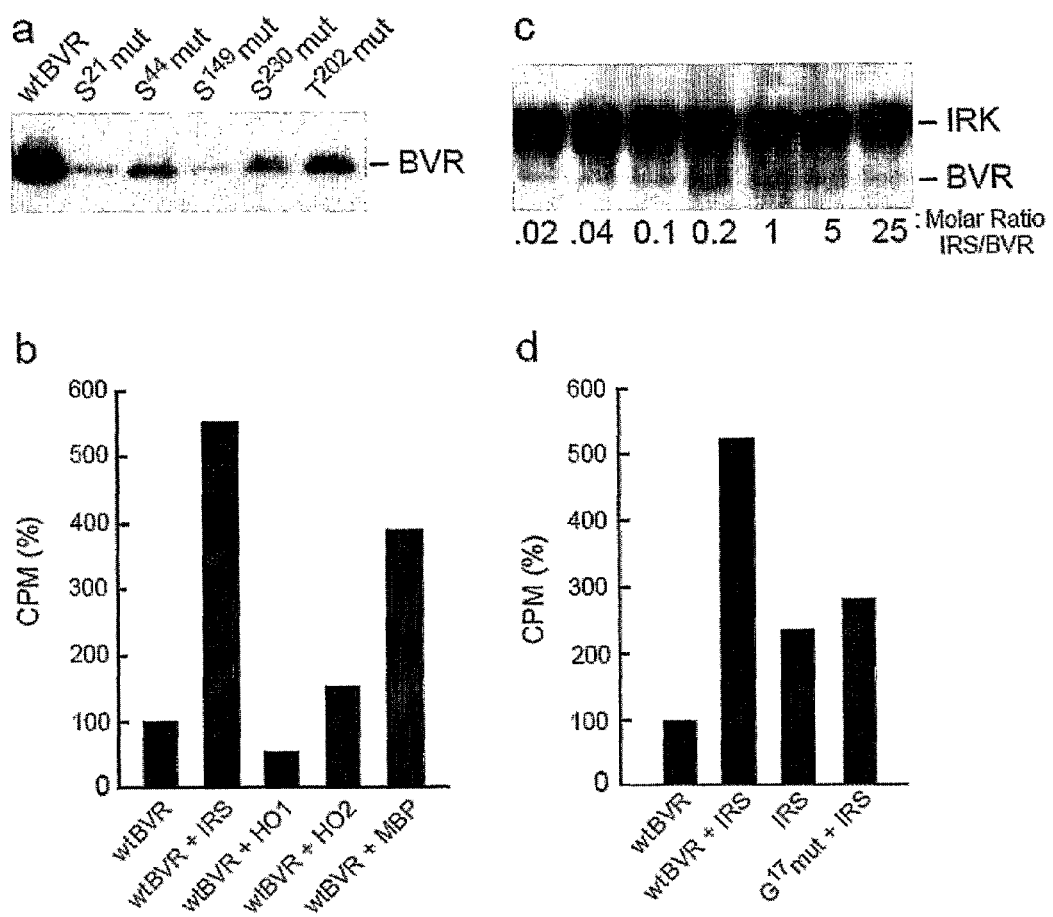
Figures 11A-D

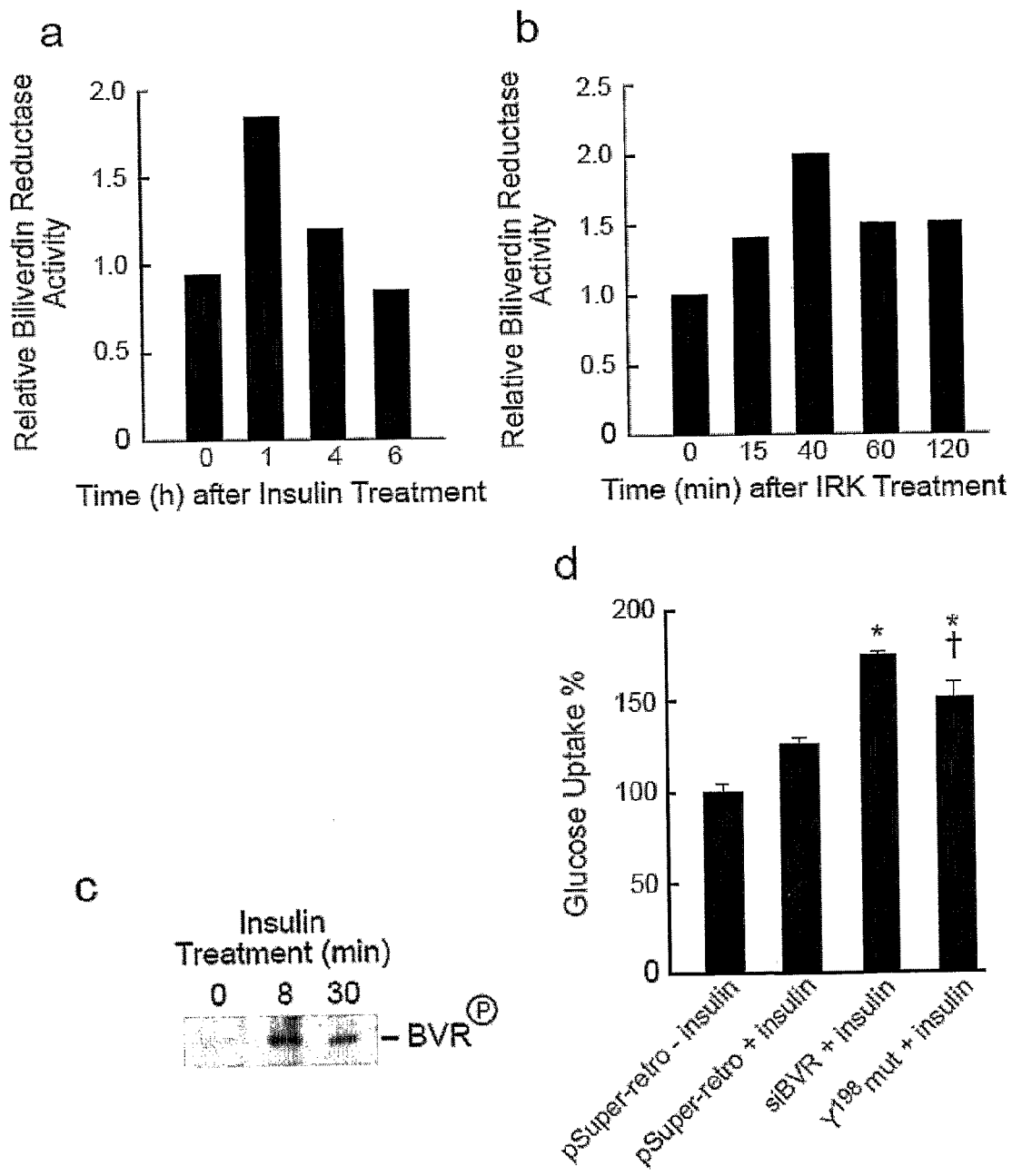
Figures 12A-D

METHODS OF MODIFYING INSULIN SIGNALING USING BILIVERDIN REDUCTASE

This application is a national stage application under 35 U.S.C. §371 of PCT/US2006/005955, filed Feb. 21, 2006, which claims the priority benefit of U.S. Provisional Patent Application Ser. No. 60/654,394, filed Feb. 18, 2005, which is hereby incorporated by reference in its entirety.

This invention was made with government support under ES004066 awarded by National Institutes of Health. The government has certain rights in this invention.

FIELD OF THE INVENTION

This invention relates to methods of modulating insulin signaling in a cell and treating a patient for a condition associated with insulin signaling.

BACKGROUND OF THE INVENTION

Biliverdin reductase (BVR) is an evolutionarily conserved soluble enzyme found primarily in mammalian species. The human reductase was recently identified as a serine/threonine kinase (Kravets et al., *J. Biol. Chem.* 279:19916-19923 (2004); Salim et al., *J. Biol. Chem.* 276:10929-34 (2001)) sharing conserved catalytic domains with known serine/threonine kinases (Hunter et al., *Annu. Rev. Biochem.* 54:897-930 (1985); Hanks et al., *Methods Enzymol.* 200:38-62 (1991)). Prior to this, the enzyme was solely considered in the context of its reductase activity and conversion of the open tetrapyrrole biliverdin to bilirubin in the cytosol (Kutty et al., *J. Biol. Chem.* 256:3956-62 (1981); Fakhrai et al., *J. Biol. Chem.* 267:4023-9 (1992); Maines et al., *Eur. J. Biochem.* 235:372-81 (1996)). Biliverdin is the product of the isomer specific cleavage of heme (Fe-protoporphyrin IX) by heme oxygenase isozymes HO-1 and HO-2 (Maines, HEME OXYGENASE: *Clinical Applications and Functions*, CRC Press Inc., Boca Raton, Fla. (1992); Maines, *Annu. Rev. Pharmacol. Toxicol.* 37:517-54 (1997)). BVR was also found to translocate into the nucleus in cells treated with cGMP (Maines et al., *J. Pharmacol. Exp. Ther.* 296:1091-7 (2001)) and function as a transcription factor for AP-1 regulated genes (Kravets et al., *J. Biol. Chem.* 279:19916-19923 (2004); Ahmad et al., *J. Biol. Chem.* 277:9226-32 (2002)). Activation of c-jun and CREB/ATF-2 by human BVR was more recently reported (Kravets et al., *J. Biol. Chem.* 279:19916-19923 (2004)).

Protein tyrosine kinases (PTK) are a multigenic family exclusive to the higher organisms (Hunter et al., *Annu. Rev. Biochem.* 54:897-930 (1985); Robinson et al., *Oncogene* 19:5548-57 (2000)). They function in cell signaling pathways involved in growth, differentiation and mobility of cells, and in development of diseases such as diabetes and cancer.

The action of insulin as a metabolic regulator and a growth factor is PTK-dependent and is an essential step in the initiation of signaling cascade, which is the coupling of the intracellular kinase domain of the insulin receptor ("IRK") with insulin receptor substrate ("IRS") (Cai et al., *J. Biol. Chem.* 278:25323-30 (2003); Grusovin et al., *Front. Biosci.* 8:d620-41 (2003); Lavan et al., *J. Biol. Chem.* 272:21403-7 (1997); Rocchi et al., *Mol. Endocrinol.* 12:914-23 (1998); White et al., *Curr. Top. Microbiol. Immunol.* 228:179-208 (1998)). Autophosphorylation on tyrosine residues and activation of IRK that results from conformational change in the kinase, following insulin binding to the extracellular domain of the receptor, serves as a recognition signal for IRS proteins (IRS-1-IRS-7) (Myers et al., *Mol. Cell. Biol.* 16:4147-55 (1996); Songyang et al., *Mol. Cell. Biol.* 14:2777-85 (1994); White, *Am. J. Physiol. Endocrinol. Metab.* 283:E413-22 (2002)).

Insulin signaling is inhibited by IRS-1 serine phosphorylation. In human IRS-1, a number of serines have been identified as the important residues, including $Ser^{307,312}$ and $Ser^{616}$. A number of serine/threonine kinases, including JNK and PKC, are known to phosphorylate IRS-1 (Aguirre et al., *J. Biol. Chem.* 275:9047-54 (2000); De Fea et al., *J. Biol. Chem.* 272:31400-6 (1997); Jakobsen et al., *J. Biol. Chem.* 276:46912-6 (2001); Kim et al., *Biol. Chem.* 384:143-50 (2003); Lee et al., *J. Biol. Chem.* 278:2896-902 (2003); Liu et al., *J. Biol. Chem.* 276:14459-65 (2001); Ozes et al., *Proc. Natl. Acad. Sci. USA* 98:4640-5 (2001); Yuan et al., *Science* 293:1673-7 (2001)). Serine phosphorylation of IRS-1 has been considered as a mechanism for insulin resistance (Tanti et al., *J. Biol. Chem.* 269:6051-7 (1994)).

Despite these advances in understanding the mechanism by which insulin resistance may occur, there remains a need to identify other kinases that can regulate insulin receptor signaling via the IRS proteins. The identification of new molecular mechanisms that can be manipulated to control insulin signaling and, consequently, glucose metabolism is highly desirable.

The present invention is directed to overcoming these and other limitations in the art.

SUMMARY OF THE INVENTION

A first aspect of the present invention relates to a method of modulating insulin signaling in a cell that includes modifying the nuclear or cellular concentration of biliverdin reductase, or fragments or variants thereof, in a cell, whereby a change in nuclear or cellular concentration of biliverdin reductase, or fragments or variants thereof, modulates insulin signaling in the cell via biliverdin reductase interaction with one or both of insulin receptor kinase domain and insulin receptor substrate.

A second aspect of the present invention relates to a method of treating a condition associated with insulin signaling that includes performing the method according to the first aspect of the present invention in a cell in vivo, thereby altering insulin signaling in the cell to treat a condition associated with insulin signaling.

A third aspect of the present invention relates to a method of treating a patient for a condition associated with insulin-mediated glucose uptake that includes the step of: administering to a patient having a condition associated with insulin-mediated glucose uptake an effective amount of a nucleic acid that inhibits native biliverdin reductase expression or activity, wherein decreased native biliverdin reductase expression or activity promotes insulin-mediated glucose uptake by cells, and effectively treats a condition associated with insulin-mediated glucose uptake.

A fourth aspect of the present invention relates to use of a nucleic acid that inhibits native biliverdin reductase expression in the manufacture of a medicament for treatment of a condition associated with insulin-mediated glucose uptake.

A fifth aspect of the present invention relates to use of a variant biliverdin reductase lacking a functional nucleotide binding domain in the manufacture of a medicament for treatment of a condition associated with insulin-mediated glucose uptake.

The present application identifies BVR as a new member of IRK substrate family and has characterized tyrosine $Y^{198}$ in YMKM, $Y^{228}$ in YLSF, and $Y^{291}$ in YCCS as IRK phosphorylation sites; tyrosine residue in positions 72 and 83 are autophosphorylated. These findings define human BVR as a member of the rare family of dual specificity (serine/threonine/tyrosine) kinases. Data presented herein demonstrate that both the tyrosine and the serine/threonine kinase activity of BVR contribute to the action of insulin and glucose uptake. As demonstrated in the accompanying Examples, the presence of IRS-1 increases phosphorylation of BVR by IRK, BVR directly phosphorylates IRS-1 on serine residues known to negatively affect glucose uptake, and insulin-mediated glucose uptake is increased when BVR expression is knocked down using siRNA directed against BVR. Together, these data indicate that BVR very likely plays a role in the mechanism of insulin resistance. Therefore, the use of BVR, BVR derived peptides, and inhibitors of native BVR expression (including gene therapy approaches) are contemplated for modifying glucose uptake and insulin receptor activity (particularly on the insulin receptor substrate).

BRIEF DESCRIPTION OF THE DRAWINGS

FIG. 1 is a ClustalW multiple sequence alignment of human BVR (SEQ ID NO: 1), pig BVR (SEQ ID NO: 2), mouse BVR (SEQ ID NO: 3), rat BVR (SEQ ID NO: 4), and chimp BVR (SEQ ID NO: 5). The alignment was made using sequences obtained from Genbank Accession Nos. NM_000712 (human), BC052146 (mouse), NM_053850 (rat), and XP_519058 (chimp), respectively. The pig BVR sequence was obtained from the Maines laboratory (previously unreported). The ClustalW alignment was performed using the default settings. The results of the alignment demonstrate that the mammalian BVR sequences are highly conserved, with the human BVR sharing about 98, 82, and 81 percent identity, respectively, with the pig, rat, and mouse BVR sequences. The human BVR sequence shares about 98 percent identity with the partial chimp BVR sequence (i.e., over the length of the partial chimp sequence). The pig BVR sequence shares about 83 and 82 percent identity with the rat and mouse BVR sequences, respectively; and about 99 percent identity with the partial chimp BVR sequence. The rat and mouse BVR sequences share about 88 percent identity; and about 82 and 81 percent identity, respectively, with the partial chimp BVR sequence. Identity and conservation among residues is denoted by the symbols beneath the alignment, where (*) denotes identity among aligned residues, (:) denotes conserved substitutions among aligned residues, and (.) denotes semi-conserved substitutions among the aligned residues. Conserved tyrosine IRK phosphorylation sites are shaded.

FIG. 2 illustrates a nucleotide sequence encoding human BVR (SEQ ID NO: 6). This sequence was obtained from Genbank Accession NM_000712, which is hereby incorporated by reference in its entirety.

FIG. 3 illustrates a nucleotide sequence encoding rat BVR (SEQ ID NO: 7). This sequence was obtained from Genbank Accession NM_053850, which is hereby incorporated by reference in its entirety.

FIG. 4 illustrates a nucleotide sequence encoding pig BVR (SEQ ID NO: 8). This sequence, previously unreported, was obtained from PCR amplified cDNA isolated in the Maines laboratory.

FIG. 5 illustrates a partial nucleotide sequence encoding the C-terminal half of chimp BVR (SEQ ID NO: 9). This sequence was obtained by assembly of exons identified at Genbank Accession NW_108910, which is hereby incorporated by reference in its entirety.

FIGS. 7A-B illustrate BVR as a substrate for insulin receptor kinase. FIG. 7A shows a time course of BVR phosphorylation by IRK. 10 µg purified wtBVR was incubated in 100 µl kinase assay buffer (pH 8.0) containing 0.1 µg IRK, 10 µM ATP, and 20 µCi [$^{32}$P]-ATP at 25° C. up to 4 h. The reaction was terminated by the addition of Laemmli buffer at different points of time as indicated. Samples were separated using 8% SDS-PAGE gel and transferred onto PVDF filter, and phosphorylated protein bands were visualized by autoradiography. FIG. 7B illustrates that IRK phosphorylates BVR on tyrosine residues. 5 µg purified wtBVR was incubated in IRK phosphorylation buffer at 30° C. for 2 h. From left to right lane 1, wtBVR plus IRK in the presence of 50 mM EDTA (pH 8.0); lane 2, wtBVR plus IRK; lane 3, wtBVR in the absence of IRK. The reaction mixtures were subjected to SDS-PAGE electrophoresis and transferred onto a polivenylidene fluoride ("PVDF") filter. The blot was immuno-stained with anti-phosphotyrosine antibodies and ECL detection system was used to visualize phosphorylated tyrosines.

FIGS. 8A-D show that BVR $Y^{198}$ residue is a target site for IRK phosphorylation. In FIG. 8A the $Y^{198}$ residue of BVR is phosphorylated by IRK. Purified wtBVR and $Y^{198}$ mutant BVR were incubated with IRK at 30° C. for 2 h. Samples were subjected to SDS-PAGE electrophoresis and processed as described in FIG. 8B. FIG. 8B is a time course of $Y^{198}$ mutant BVR phosphorylation by IRK. A purified preparation of human BVR that carried $Y^{198}$ mutation was incubated with IRK for up to 3 h as described in FIG. 7A. Samples taken at the indicated time-points were analyzed for detection of phosphorylated proteins as above. FIG. 8C is a graph showing the effect of mutation of tyrosine residues on BVR phosphorylation by IRK. 5 µg of purified wtBVR or the above indicated BVR tyrosine mutants were incubated with IRK for 2 h at 30° C. in the presence of γ[$^{32}$P]-ATP as described in the text. Subsequently, samples were subjected to SDS-PAGE, stained with Coomassie blue and visualized bands were excised and used for measurement of radioactive content. The experiments were repeated three times. FIG. 8D shows further identification of BVR tyrosine residues phosphorylated by IRK. The indicated double mutants of BVR were used as substrates for IRK and analysis was carried out as in FIG. 8A.

FIGS. 9A-B demonstrate that human BVR autophosphorylates on tyrosine residues and is a tyrosine kinase. In FIG. 9A, effect of tyrosine mutations of BVR on its autophosphorylation is shown. Human wtBVR and BVR with mutations in tyrosine were used in the experiment to determine autophosphorylation of BVR. The reactions were performed as described in the Examples. FIG. 9B is a graph showing that BVR tyrosine kinase activity was checked by incubating 5 µg purified BVR with 5 µg Raytide in 50 µl kinase buffer containing 10 µM labeled ATP for 2 h at 30° C. The aliquots of the reaction were transferred onto P81 Whatman filters and radioactivity due to phosphorylation was measured using a scintillation counter.

FIGS. 10A-B illustrate that autophosphorylation of BVR is an $Mn^{+2}$ dependant kinase reaction. FIG. 10A shows metal dependence of BVR kinase activity. The effects of different metal ions (30 mM $MnCl_2$, 20 mM $MgCl_2$, 20 mM $CaCl_2$, 20 mM Zn acetate) and their combinations were analyzed as indicated in the text. FIG. 10B shows inhibition of BVR autophosphorylation by a PTK inhibitor. Phosphorylation of wtBVR by IRK in the presence of tyrosine kinase inhibitor genestein (200 µM); DMSO was used as the vehicle for genestein and was included in the control reaction mixture. The reactions were carried out in HEPES buffer (pH 8.0) in the presence of 20 mM $MgCl_2$ as described in the Examples.

FIGS. 11A-D demonstrate that human BVR is a kinase for IRS. FIG. 11A shows that identification of serine residues target BVR autophosphorylation. BVR containing mutations on threonine 202 and serine residues, as indicated in the figure, were subjected to autophosphorylation analysis as described in the text. As shown in FIG. 11B, IRS-1 is a substrate for BVR. 5 µg purified BVR was incubated with 5 µg IRS-1 or HO-1 or HO-2, used as a control for kinase activity, and MBP which was used as the substrate control in 50 µl kinase buffer as described in the Examples. As shown in FIG. 11C, IRS presence increases phosphorylation of BVR by IRK. Phosphorylation of BVR by IRK was examined in the presence of increasing molar ratio of IRS/BVR as indicated in the figure. As shown in FIG. 11D, ATP binding ability of BVR is necessary for IRS-1 phosphorylation by BVR. Mutant $G^{17}$ was compared with wtBVR as a kinase for IRS.

FIG. 12A-D illustrates that "knock-down" BVR and $Y^{198}$ detection increased glucose uptake into 293A cells upon insulin induction. As shown in the graph of FIG. 12A, insulin treatment increases BVR activity. 293A cells were treated with insulin (50nM) and subsequently used at indicated time points for BVR activity measurement. As shown in FIG. 12B, BVR phosphorylation by IRK in vitro increases BVR reductase activity. Purified BVR was phosphorylated by IRK for the indicated periods. Reactions were terminated by diluting with PBS and freezing at −20° C. BVR activity was determined as in FIG. 12A, and normalized to that of the control (43.8 µmol per min per mg). As shown in FIG. 12C, insulin treatment increases BVR tyrosine phosphorylation. 293A cells were incubated with insulin and after 8 min or 30 min, subjected to immunoprecipitation using anti-human BVR antibodies. The phosphorylated BVR was visualized by immunoblotting using anti-tyrosine antibodies. ECL system was used for visualization of phosphorylated BVR. In FIG. 12D, the effect of insulin treatment on glucose uptake cells infected with siBVR or $Y^{198}$ mutant BVR were treated with insulin for 15 min and subsequently incubated in 1 ml PBS containing 5 mM glucose and 1 µCi/ml-2-deoxy-1 [3H] glucose (2DG) for 15 min. Cells were washed with cold PBS and lysed by addition of 1% (w/v) SDS to each well. Glucose uptake assay was performed by measuring [$^3$H]-2DG uptakes as described in the Examples. Experiments were carried out in triplicate and repeated three times. Data are presented as mean±SD of three experiments.

DETAILED DESCRIPTION OF THE INVENTION

Figure 6:
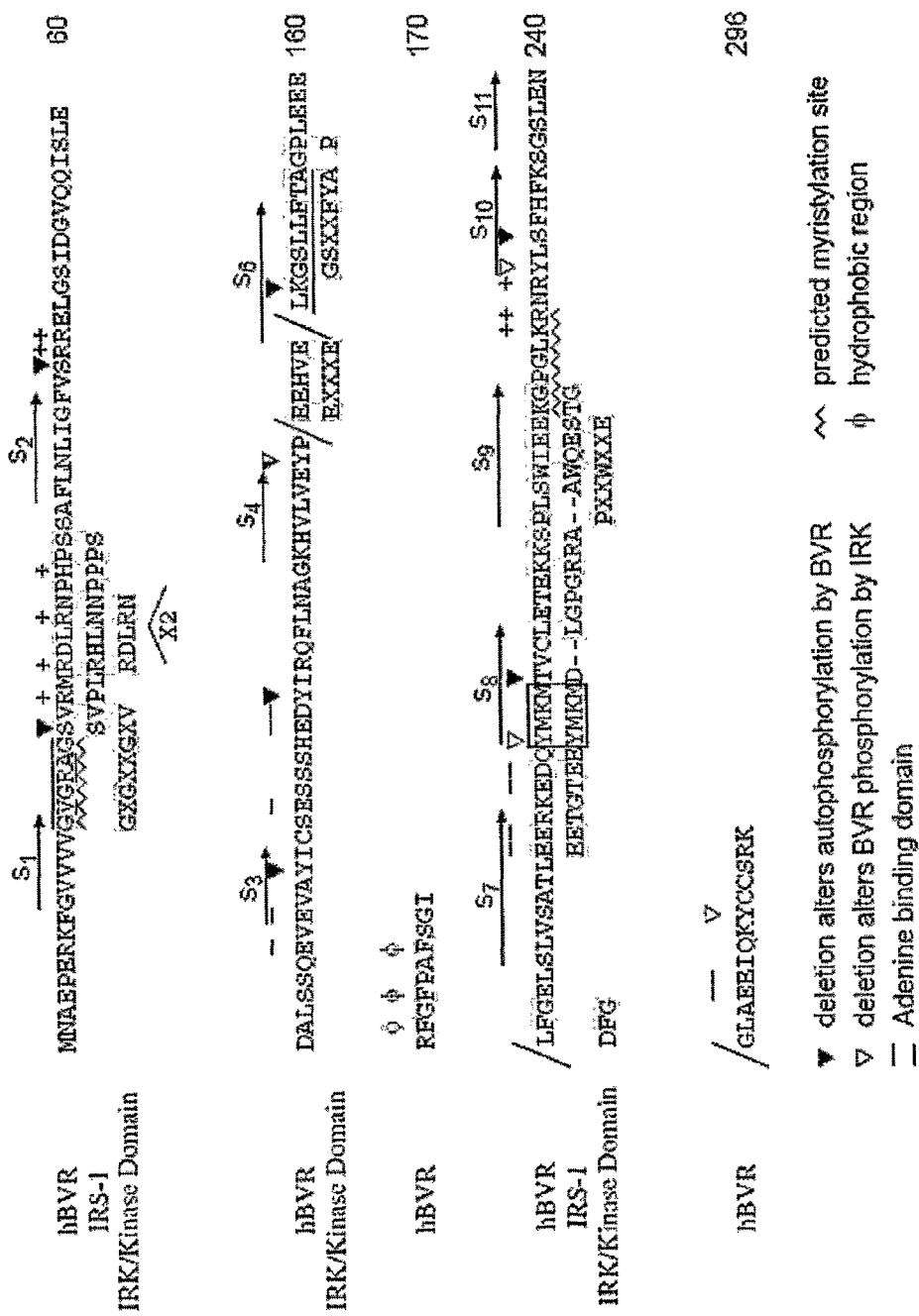
FIG. 6 is a sequence alignment of human BVR (SEQ ID NO: 1) showing residues that share similarity to IRK and IRS-1 residues that are phosphorylated.

The present invention relates to the use of biliverdin reductase ("BVR") expression levels to regulate insulin signaling. As a consequence, by modifying the nuclear or cellular concentration of BVR, or fragments or variants thereof, insulin signaling can be regulated, i.e., either enhanced or suppressed, to effect glucose uptake by the cell.

Consequently, a further aspect of the present invention relates to methods of treating a mammalian patient for conditions associated with insulin signaling. Suitable patients can be any mammal, but preferably a human, non-human primate (ape, chimp, orangutan, etc.), rodent (e.g., mouse, rat, guinea pig, etc.), cow, horse, sheep, pig, llama, goat, deer, elk, bison, etc.

By modifying the nuclear or cellular concentration of BVR, or fragments or variants thereof, in a cell, in accordance with the present invention, a condition associated with insulin signaling can be treated. Exemplary conditions associated with insulin signaling include, without limitation, hyperinsulinemia and disorders which implicate the same, such as hypertension, hyperlipidemia and arteriosclerosis, in addition to obesity and diabetes (type II). It is believed that the present invention affords both therapeutic and prophylactic treatments that can minimize side effects associated with these conditions or disorders.

To increase the nuclear or cellular concentration of BVR, or fragments or variants thereof, either BVR or the fragments or variants thereof can be introduced into the cell directly or expressed therein via in vivo cell transformation. To decrease the nuclear concentration of BVR, inhibitory BVR RNA can be introduced into the cell directly or expressed therein via in vivo transformation, which inhibitory BVR RNA inhibits BVR mRNA translation. The inhibitory BVR RNA can either be in the form of antisense RNA or interfering RNA molecules (RNAi's) that target (or bind to) BVR transcripts. These interfering BVR RNA molecules may be introduced into the cell directly or expressed therein via in vivo transformation to inhibit BVR expression/activity. An alternative to inhibiting BVR expression, BVR fragments or variants that are unable to phosphorylate IRS (e.g., IRS-1) can be used to reduce the activity of fully functional (i.e., native) BVR. The BVR fragments or variants can also be introduced into the cell directly or expressed therein via in vivo transformation. Thus, both protein or RNA delivery systems and gene delivery systems can be employed in the present invention.

As used herein, the terms biliverdin reductase and BVR refer to any mammalian BVR, but preferably human BVR ("hBVR"). One form of hBVR has an amino acid sequence corresponding to SEQ ID NO: 1 as illustrated in FIG. 1. Heterologous expression and isolation of HBVR is described in Maines et al., *Eur. J. Biochem.* 235:372-381 (1996); Maines et al., *Arch. Biochem. Biophys.* 300:320-326 (1993), each of which is hereby incorporated by reference in its entirety. A DNA molecule encoding this form of HBVR has a nucleotide sequence corresponding to SEQ ID NO: 6 as illustrated in FIG. 2.

Another form of hBVR is reported at Komuro et al., Genbank Accession No. G02066, direct submission to the EMBL Data Library (1998), which is hereby incorporated by reference in its entirety. Differences between the hBVR of SEQ ID NO: 1 and the hBVR of Komuro et al. are at aa residues 3, 154, 155, and 160. Specifically, residue 3 can be either alanine or threonine, residue 154 can be either alanine or serine, residue 155 can be either aspartic acid or glycine, and residue 160 can be either aspartic acid or glutamic acid.

In addition, BVR from other mammals have been recombinantly expressed and isolated, including without limitation rat, mouse, pig, and chimp.

One form of rat biliverdin reductase ("rBVR") has an amino acid sequence corresponding to SEQ ID NO: 3 as illustrated in FIG. 1. Heterologous expression and isolation of rBVR is described in Fakhrai et al., *J. Biol. Chem.* 267(6): 4023-4029 (1992), which is hereby incorporated by reference in its entirety. The rBVR of SEQ ID NO: 3 shares about 82% aa identity to the hBVR of SEQ ID NO: 1, with variations in aa residues being highly conserved. The DNA molecule encoding this form of rBVR has a nucleotide sequence corresponding to SEQ ID NO: 7 as illustrated in FIG. 3.

One form of mouse biliverdin reductase ("mBVR") is reported at Genbank Accession NP_080954, and has an amino acid sequence according to SEQ ID NO: 4 as illustrated in FIG. 1. The mBVR sequence is about 81 percent identical to the HBVR sequence of SEQ ID NO: 1.

One form of pig biliverdin reductase ("pBVR") has been isolated and sequenced. This form of pBVR has an amino acid sequence according to SEQ ID NO: 2 as illustrated in FIG. 1. This pBVR sequence is about 98 percent identical to the HBVR sequence of SEQ ID NO: 1. The DNA molecule encoding this form of pBVR has a nucleotide sequence corresponding to SEQ ID NO: 8 as illustrated in FIG. 4.

A partial amino acid sequence of the chimp BVR ("cBVR") has been isolated and sequenced. This form of cBVR has a partial amino acid sequence according to SEQ ID NO: 5 as illustrated in FIG. 1. The cBVR sequence is about 98 percent identical to the hBVR sequence of SEQ ID NO: 1 (i.e., over the length of the chimp sequence). The DNA molecule encoding this form of cBVR has a partial nucleotide sequence corresponding to SEQ ID NO: 9 as illustrated in FIG. 5. FIG. 1 shows that the chimp sequence is missing its N-terminal sequence. The missing N-terminal portion of this sequence can be obtained easily by performing PCR to amplify the genomic cBVR nucleic acid sequence using a series of redundant forward and reverse primers encoding the N-terminal MNAEP residues and the MTLSL residues, respectively. Once the amplified sequences are recovered, redundant sequencing efforts can be used to obtain a consensus of the N-terminal portion, which can be combined with the partial sequences of SEQ ID NO: 9. The resulting translation product can be combined with the partial amino acid sequence of SEQ ID NO: 5 to obtain the full-length cBVR amino acid sequence.

In addition to mammalian BVR, the present invention also contemplates use of a non-mammalian BVR that is sufficiently homologous to the mammalian BVR described above, and preferably contains one or more of the tyrosine phosphorylation domains that can be phosphorylated by IRK, most preferably the YMXM domain. Non-mammalian BVR sequences can be identified by similar homology search to human BVR, particularly using BLAST or motif searches for those regions highly conserved between the two BVR sequences.

As described in greater detail in co-pending U.S. patent application Ser. No. 09/606,129 to Maines, filed Jun. 28, 2000 (which is hereby incorporated by reference in its entirety), BVR is characterized by a large number of functional domains and motifs, including without limitation: putative and/or demonstrated phosphorylation sites (including those illustrated in FIG. 6); a basic N-terminal domain characterized by aa 6 to 8 of SEQ ID NO: 1; a hydrophobic domain characterized by aa 9 to 14 of SEQ ID NO: 1; a nucleotide (adenine) binding domain characterized by aa 15 to 20 of SEQ ID NO: 1; an oxidoreductase domain characterized by aa 90 to 97 of SEQ ID NO: 1; a leucine zipper spanning aa 129 to 157 of SEQ ID NO: 1; several kinase motifs, including aa 44 to 46, aa 147 to 149, and aa 162 to 164 of SEQ ID NO: 1; a nuclear localization signal spanning aa 222 to 228 of SEQ ID NO: 1; a number of myristylation sites (including those illustrated in FIG. 6); a zinc finger domain spanning aa 280 to 293 of SEQ ID NO: 1; and several substrate binding domains, such as a protein kinase C ("PKC") binding domain, an insulin receptor substrate ("IRS") binding domain, and an IRK binding domain. These domains are either identical or highly conserved among the above-identified BVR of SEQ ID NOs: 1-5.

Analysis of the primary and the recently solved secondary structures of BVR (Fakhrai et al., *J. Biol. Chem.* 267:4023-9 (1992); Maines et al., *Eur. J. Biochem.* 235:372-81 (1996); Whitby et al., *J. Mol. Biol.* 319:1199-210 (2002), each of which is hereby incorporated by reference in its entirety) identifies features that signify its relevance to PTK regulated functions and contribution to cell signaling as an adaptor/scaffold protein (FIG. 6). This includes the $Y^{198}$MKM sequence that in IRS proteins functions as a binding site for effector proteins with Src homology-2 (SH-2) domain such as phosphatidylinositol (PI) 3-kinase (Myers et al., *Mol. Cell.* *Biol.* 16:4147-55 (1996); Songyang et al., *Mol. Cell. Biol.* 14:2777-85 (1994), each of which is hereby incorporated by reference in its entirety). The residues that flank the sequence closely resemble the YMXM sequences of IRS-1; in both, four acidic residues are located N terminal to the tyrosine, a feature frequently associated with the tyrosine residues that are substrate for PTKs (Hunter et al., *Annu. Rev. Biochem.* 54:897-930 (1985), which is hereby incorporated by reference in its entirety). In BVR a threonine residue, and in IRS-1 a serine residue, flanks the C terminal of the second methionine. In addition, partial sequence alignment of IRK and BVR show a similarity of key functional residues in corresponding regions. As shown in FIG. 6, these include, inter alia, the adenine binding domain (GXGXXG) and the serine/threonine kinase domain (G-S/T-XX-F/Y-XAP). In addition, the crystal structure of the rat enzyme (Whitby et al., *J. Mol. Biol.* 319:1199-210 (2002), which is hereby incorporated by reference in its entirety) reveals structural features of BVR that are consistent with its function as an adaptor/scaffolding protein. While the N terminal lobe of BVR possesses a nucleotide binding domain, the C terminus contains a six stranded β sheet that would provide an ideal docking and protein:protein interaction site. Furthermore, as demonstrated in the Examples with immunoblot analysis of BVR purified from human or rat liver, using anti-phosphotyrosine antibodies as the probe, one or more of six HBVR tyrosine residues is phosphorylated.

As used herein, BVR variants and fragments can be substituted for BVR either in whole or in part.

Subclones of a gene encoding a known BVR can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

In another approach, based on knowledge of the primary structure of the protein, fragments of a BVR gene may be synthesized using the PCR technique together with specific sets of primers chosen to represent particular portions of the protein (Erlich et al., *Science* 252:1643-51 (1991), which is hereby incorporated by reference in its entirety). These can then be cloned into an appropriate vector for expression of a truncated protein or polypeptide from bacterial cells as described above. For example, oligomers of at least about 15 to 20 nt in length can be selected from the nucleic acid molecule of SEQ ID NO: 6 (FIG. 4) for use as primers.

In addition, chemical synthesis can also be employed using techniques well known in the chemistry of proteins such as solid phase synthesis (Merrifield, *J. Am. Chem. Assoc.* 85:2149-2154 (1964), which is hereby incorporated by reference in its entirety) or synthesis in homogenous solution (Houbenweyl, *Methods of Organic Chemistry*, ed. E. Wansch, Vol. 15, I and II, Thieme, Stuttgart (1987), which is hereby incorporated by reference in its entirety).

Exemplary fragments include N-terminal, internal, and C-terminal fragments that possess IRK phosphorylation sites. Preferred fragments lack the adenine binding domain.

Variants of suitable BVR proteins or polypeptides can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of BVR. According to one embodiment, the adenine binding domain is rendered non-functional, in which case the BVR can be used as a substrate by IRK, but the BVR is incapable of phosphorylating IRS (e.g., IRS-1).

Variants of BVR can also be fragments of BVR that include one or more deletion, addition, or alteration of amino acids of the type described above. The BVR variant preferably contains a deletion, addition, or alteration of amino acids within one of the above-listed functional domains. The substituted or additional amino acids can be either L-amino acids, D-amino acids, or modified amino acids, preferably L-amino acids. Whether a substitution, addition, or deletion results in modification of BVR variant activity may depend, at least in part, on whether the altered amino acid is conserved. Conserved amino acids can be grouped either by molecular weight or charge and/or polarity of R groups, acidity, basicity, and presence of phenyl groups, as is known in the art.

Variants can include the protein or polypeptides of SEQ ID NOS: 1-5 and Komuro et al., which have single or multiple amino acid residue substitutions. Exemplary variants include, without limitation, SEQ ID NO: 1 as modified by one or more of the following variations: (i) $Gly^{17}$-to-Ala within the nucleotide binding domain, (ii) $Ser^{44}$-to-Ala within one of the kinase motifs, (iii) $Cys^{74}$-to-Ala within a substrate binding domain, (iv) $Lys^{92}His^{93}$-to-Ala-Ala within the oxidoreductase motif, (v) $G^{222}LKRNR^{227}$-to-VIGSTG within the nuclear localization signal, and (vi) $Cys^{281}$-to-Ala within the zinc finger domain, and $Lys^{296}$-to-Ala at the C terminus within a substrate binding domain (i.e., protein kinase inhibitory domain). Similar variants of SEQ ID NOS: 2-5 are also contemplated. Other variants are described in the accompanying examples.

One preferred variant, identified as (i) above, contains a non-functional nucleotide binding domain. As a consequence, these variants cannot phosphorylate other proteins, including IRS.

Another preferred variant, identified as (iv) above, lacks a functional oxidoreductase domain, and cannot participate in NADH- or NADPH-dependent conversion of biliverdin to bilirubin.

Another preferred variant possesses both variation (i) and variation (iv) as described above.

Variants may also include, for example, a polypeptide conjugated to a signal (or leader) sequence at the N-terminal end of the protein which co-translationally or post-translationally directs transfer of the protein. The polypeptide may also be conjugated to a linker or other sequence for ease of synthesis, purification, identification, or therapeutic use (i.e., delivery) of the polypeptide.

Another variant type of BVR is a fusion polypeptide that includes a fragment of BVR containing the YMKM motif. The fusion protein can be expressed or synthesized using an in-frame gene fusion according to known techniques in the art. The BVR fragment can be coupled to a cytoplasmic localization signal. A number of cytoplasmic localization signals have been identified in the art and can be utilized in combination with the fragment of BVR to obtain the fusion protein.

It is to be understood that the present invention contemplates the use of any mammalian or non-mammalian BVR sequence in the formation of the chimeric genes and expression systems of the present invention. Homologous BVR polypeptides from mammals and non-mammals other than those described above are preferably characterized by an amino acid identity of at least about 60 percent, more preferably at least about 70 percent or 80 percent, most preferably at least about 85 percent or 90 percent or 95 percent as compared to the BVR of SEQ ID NOS: 1-5. Other mammalian and non-mammalian cDNA molecules can be identified based upon their alignment with the BVR cDNA of SEQ ID NOS: 6-9, where such alignment preferably is at least about 60 percent identical (more preferably at least about 70 percent, 75 percent, 80 percent, 85 percent, 90 percent, or 95 percent identical). Alternatively, other mammalian BVR encoding cDNA molecules can be identified by the ability of mammalian cDNA sequences to hybridize to the complement of SEQ ID NOS: 6-9, respectively, under stringent hybridization and wash conditions. Exemplary stringent hybridization and wash conditions include, without limitation, hybridization at 50° C. or higher (i.e., 55° C., 60° C., or 65° C.) in a hybridization medium that includes 0.9× (or higher, such as 2× or 5×) sodium citrate ("SSC") buffer, followed by one or more washes at increasing stringency using 0.2×SSC buffer at temperatures from 42° C. up to the temperature of the hybridization step. Higher stringency can readily be attained by increasing the temperature for either hybridization or washing conditions or decreasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency.

The BVR protein or polypeptide (or fragment or variant thereof) can be recombinantly produced, isolated, and then purified, if necessary. When recombinantly produced, the biliverdin reductase protein or polypeptide (or fragment or variant thereof) is expressed in a recombinant host cell, typically, although not exclusively, a prokaryote.

When a prokaryotic host cell is selected for subsequent transformation, the promoter region used to construct the recombinant DNA molecule (i.e., transgene) should be appropriate for the particular host. The DNA sequences of eukaryotic promoters, as described infra for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Mammalian cells can also be used to recombinantly produce BVR or fragments or variants thereof. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells.

Suitable expression vectors for directing expression in mammalian cells generally include a promoter, as well as other transcription and translation control sequences known in the art. Common promoters include SV40, MMTV, metallothionein-1, adenovirus Ela, CMV, immediate early, immunoglobulin heavy chain promoter and enhancer, and RSV-LTR.

Regardless of the selection of host cell, once the DNA molecule coding for a biliverdin reductase protein or polypeptide (or fragment or variant thereof) or inhibitory RNA molecule, has been ligated to its appropriate regulatory regions (or chimeric portions) using well known molecular cloning techniques, it can then be introduced into a suitable vector or otherwise introduced directly into a host cell using transformation protocols well known in the art (Sambrook et al., *Molecular Cloning: A Laboratory Manual*, Second Edition, Cold Spring Harbor Press, NY (1989), which is hereby incorporated by reference in its entirety).

When an expression vector is used for purposes of in vivo transformation to induce or inhibit BVR expression in a target cell, promoters of varying strength and specificity can be employed depending on the degree of enhancement of suppression desired.

One of skill in the art can readily select appropriate constitutive mammalian promoters based on their strength as a promoter.

As an alternative to constitutive promoters, a mammalian tissue-specific promoter can be utilized. Any of a variety of tissue specific promoters are known in the art and can be selected based upon the tissue or cell type to be treated.

Muscle-specific promoters can be smooth muscle-specific, skeletal muscle-specific, or cardiac muscle-specific. Exemplary muscle-specific promoters include, without limitation, PGC-1α promoter (U.S. Patent Application 20060035849 to Spiegelman et al., which is hereby incorporated by reference in its entirety); creatine kinase promoter (Sun et al., *Mol. Ther.* 11(6):889-98 (2005), which is hereby incorporated by reference in its entirety); mef2c promoter (Heidt et al., *Genesis* 42(1):28-32 (2005), which is hereby incorporated by reference in its entirety); MuSK promoter (Tang et al., *J. Biol. Chem.* 281(7):3943-53 (2006), which is hereby incorporated by reference in its entirety).

Exemplary neuron specific promoters include, without limitation, Thy1 promoter (Vidal et al., *EMBO J.* 9:833-840 (1990); Eckenstein et al., *Exp Neurol.* (online advance publication Feb. 15, 2006), each of which is hereby incorporated by reference in its entirety); PrP promoter (Asante et al., *Neurobiol Dis.* 10(1): 1-7 (2002), which is hereby incorporated by reference in its entirety); neuron-specific enolase promoter (Kuhn et al., *Eur. J. Neurosci.* 22(8):1907-15 (2005), which is hereby incorporated by reference in its entirety); and CaMKIIα promoter (Michalon et al., *Genesis* 43(4):205-12 (2005), which is hereby incorporated by reference in its entirety).

Exemplary liver specific promoters include, without limitation, serum amyloid P component promoter (Tanaka et al., *Metabolism* 54(11):1490-8 (2005), which is hereby incorporated by reference in its entirety); Apo-E promoter (Kakumitsu et al., *Leuk Res.* 29(7):761-9 (2005), which is hereby incorporated by reference in its entirety); alpha 1-antitrypsin (AAT) (Al-Dosari et al., *Biochem. Biophys. Res. Commun.* 339(2):673-8 (2006), which is hereby incorporated by reference in its entirety).

Exemplary kidney specific promoters include, without limitation, cadherin promoter (Yang et al., *Am. J. Physiol. Renal Physiol* online advance publication Jan. 31, 2006, which is hereby incorporated by reference in its entirety); uromodulin promoter (Huang et al., *BMC Biotechnol.* 5(1):9 (2005); Kim et al., *Transgenic Res.* 12(2):191-201 (2003), each of which is hereby incorporated by reference in its entirety); CLC-K1 and CLC-K2 promoters (Uchida et al., *Kidney Int.* 60(2):416-21 (2001), which is hereby incorporated by reference in its entirety); P1-PTHR promoter (Amizuka et al., *Endocrinology.* 138(1):469-81 (1997), which is hereby incorporated by reference in its entirety).

Other tissue-specific promoters are known in the art and can be utilized in the present invention to obtain a tissue-specific recombinant gene that encodes BVR (or fragment or variant thereof) or an inhibitory RNA molecule.

Whether the promoter is tissue-specific or not, the promoter can also be made inducible for purposes of controlling when expression or suppression of BVR is desired. One of skill in the art can readily select appropriate inducible mammalian promoters from those known in the art. One exemplary inducible promoter includes a Tet-O response element (Farson et al., *Hum. Gene Ther.* 12(8):981-97 (2001), which is hereby incorporated by reference in its entirety). When used in combination with a tissue-specific promoter, the Tet-O response elements can render a tissue-specific promoter inducible to tetracycline and its derivatives (see, e.g., Michalon et al., *Genesis* 43(4):205-12 (2005), which is hereby incorporated by reference in its entirety).

The recombinant molecule can be introduced into host cells via transformation, particularly transduction, conjugation, mobilization, or electroporation. Suitable host cells include, but are not limited to, bacteria, virus, yeast, mammalian cells, insect, plant, and the like. The host cells, when grown in an appropriate medium, are capable of expressing the biliverdin reductase (or fragment or variant thereof), which can then be isolated therefrom and, if necessary, purified. The biliverdin reductase, or fragment or variant thereof, is preferably produced in purified form (preferably at least about 60%, more preferably 80%, pure) by conventional techniques.

Modifying insulin-mediated glucose uptake in a cell may involve transforming the cell with a DNA construct which expresses inhibiting BVR RNA. The inhibitory BVR RNA can be an antisense BVR RNA, BVR siRNA, or an RNA aptamer (i.e., with or without a trans-acting ribozyme).

Basically, the antisense nucleic acid is expressed from a transgene which is prepared by ligation of a DNA molecule, coding for BVR, or a fragment or variant thereof, into an expression vector in reverse orientation with respect to its promoter and 3' regulatory sequences. Upon transcription of the DNA molecule, the resulting RNA molecule will be complementary to the mRNA transcript coding for the actual protein or polypeptide product. Ligation of DNA molecules in reverse orientation can be performed according to known techniques which are standard in the art.

Such antisense nucleic acid molecules of the invention may be used in gene therapy to treat or prevent various disorders associated with insulin-mediated glucose uptake, including but not limited to conditions associated with insulin resistance, such as type 2 diabetes, hypertension, cardiovascular disease, and obesity. For a discussion of the regulation of gene expression using anti-sense genes, see Weintraub et al., *Reviews-Trends in Genetics*, 1(1) (1986), which is hereby incorporated by reference in its entirety. As discussed infra, recombinant molecules including an antisense sequence or oligonucleotide fragment thereof, may be directly introduced into cells of tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes.

As an alternative to antisense BVR mRNA, the RNA-based form of gene-silencing known as RNA-interference (RNAi) can also be utilized. Numerous reports have been published on critical advances in the understanding of the biochemistry and genetics of both gene silencing and RNAi (Matzke et al., *Curr. Opin. Genet. Dev.* 11(2):221-227 (2001), which is hereby incorporated by reference in its entirety). In RNAi, the introduction of double stranded RNA (dsRNA, or iRNA, for interfering RNA) into the cells leads to the destruction of the endogenous, homologous mRNA, phenocopying a null mutant for that specific gene. In both post-transcriptional gene silencing and RNAi, the dsRNA is processed to short interfering molecules of 21-, 22- or 23-nucleotide RNAs (siRNA) by a putative RNAaseIII-like enzyme (Tuschl T., *Chembiochem* 2:239-245 (2001); Zamore et al., *Cell* 101:25-3, (2000), each of which is hereby incorporated by reference in its entirety). The endogenously generated siRNAs mediate and direct the specific degradation of the target mRNA. In the case of RNAi, the cleavage site in the mRNA molecule targeted for degradation is located near the center of the region covered by the siRNA (Elbashir et al., *Gene Dev.* 15(2):188-200 (2001), which is hereby incorporated by reference in its entirety). The dsRNA for the nucleic acid molecule of the present invention can be generated by transcription in vivo, which involves modifying the nucleic acid molecule encoding BVR for the production of dsRNA, inserting the modified nucleic acid molecule into a suitable expression vector having the appropriate 5' and 3' regulatory nucleotide sequences operably linked for transcription and translation, and introducing the expression vector having the modified nucleic acid molecule into a suitable host cell or subject. Alternatively, complementary sense and antisense RNAs derived from a substantial portion of the coding region of the BVR nucleic acid molecule are synthesized in vitro (Fire et al., *Nature* 391:806-811 (1998); Montgomery et al, *Proc. Natl Acad Sci USA* 95:15502-15507; Tabara et al., *Science* 282:430-431 (1998), each of which is hereby incorporated by reference in its entirety). The resulting sense and antisense RNAs are annealed in an injection buffer, and dsRNA is administered to the subject using any method of administration described herein Thus, siRNA can be used to decrease the cellular or nuclear concentration of BVR. Preferably, an siRNA is about 20-23 nucleotides in length, more preferably exactly 21 nucleotides in length. Specific siRNAs suitable for downregulating expression levels/activity of cellular BVR can be identified at the Ambion, Inc. Internet site, which provides a target sequence to siRNA converter. By introducing the cDNA sequence of BVR, the Ambion, Inc. Internet site will identify sense and anti-sense strands of the siRNA molecule, as well as identify the DNA construct needed to express the siRNA.

An exemplary siRNA sequence (in the form of a duplex) is as follows:

```
5'-UCCUCAGCGUUCCUGAACCUG;      (SEQ ID NO: 10)

3'-AGGAGUCGCAAGGACUUGGAC.      (SEQ ID NO: 11)
```

Inhibitory RNA molecules can also be RNA aptamers or multivalent RNA aptamers that can bind to and interrupt the IRK-induced phosphorylation of BVR (and subsequent IRS-1 phosphorylation and activation by the phosphorylated BVR). Inhibitory RNA aptamers and multivalent aptamers can be constructed, and indeed, chimeric genes (including multimeric genes) that express such aptamers in vivo can be constructed in accordance with the procedures described in U.S. Pat. No. 6,458,559 and U.S. patent Application No. 20050282190 to Shi and L is, each of which is hereby incorporated by reference in its entirety.

The cell in which the nuclear or cellular concentration of BVR, or fragments or variants thereof, is to be modified can be located in vivo or ex vivo. The modification of BVR nuclear or cellular concentrations can be also be used as one part of a multi-component approach for treating diseases or disorders (i.e., generally, conditions) that implicate insulin-mediated glucose uptake which can be modified by BVR. Such complimentary treatments can be any suitable therapy, whether now known or hereafter developed.

The nuclear or cellular concentration of BVR (or fragments or variants thereof) can be modified according to a number of approaches, either by delivering the BVR (or fragments or variants thereof) or inhibitory BVR RNA molecule into the cell in a manner that affords the protein or polypeptide or RNA molecule to be active within the cell, or by delivering DNA encoding BVR (or fragments or variants thereof) or inhibitory BVR RNA molecule into the cell in a manner effective to induce the expression thereof in the cell.

When BVR (or fragments or variants thereof) is delivered into target cells, it may be desirable that such delivery be effective to cause nuclear uptake of the BVR (or fragments or variants thereof). As noted above, BVR or fragments or variants may contain the native BVR nuclear localization signal or a chimeric nuclear localization signal. In another embodiment, a variant BVR (such as those described above) can be prepared so that it lacks a functional nuclear localization signal, in which case the variant will remain in the cytoplasmic fraction of a cell into which it is introduced or expressed.

When inhibitory BVR RNA is delivered into target cells, the inhibitory RNA may be effective in the cytoplasm and need not be targeted to any particular location within the cytoplasm, although higher efficacy can be obtained when targeting the inhibitory BVR RNA to ribosomal sites.

One approach for delivering therapeutic protein or polypeptides or nucleic acid molecules into cells involves the use of liposomes. Basically, this involves providing a liposome which includes that protein or polypeptide or nucleic acid to be delivered, and then contacting the target cell with the liposome under conditions effective for delivery of the protein or polypeptide or nucleic acid into the cell.

Liposomes are vesicles comprised of one or more concentrically ordered lipid bilayers which encapsulate an aqueous phase. They are nommally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), each of which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

Like liposomes, micelles have also been used in the art for drug delivery. A number of different micelle formulations have been described in the literature for use in delivery proteins or polypeptides, and others have been described which are suitable for delivery of nucleic acids. Any suitable micelle formulations can be adapted for delivery of the therapeutic protein or polypeptide or nucleic acids of the present invention. Exemplary micelles include without limitation those described, e.g., in U.S. Pat. No. 6,210,717 to Choi et al.; and U.S. Pat. No. 6,835,718 to Kosak, each of which is hereby incorporated by reference in its entirety.

An alternative approach for delivery of proteins or polypeptides or nucleic acids involves the conjugation of the desired therapeutic agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety. The siRNA molecule can also be present in the form of a bioconjugate, for example a nucleic acid conjugate as described in U.S. Pat. Nos. 6,528,631, 6,335,434, 6,235,886, 6,153,737, 5,214,136, or 5,138,045, each of which is hereby incorporated by reference in its entirety.

Stable formulations for delivery of siRNA can be formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see, e.g., Ogris et al., *AAPA Pharm Sci* 3:1-11 (2001); Furgeson et al., *Bioconjugate Chem.*, 14:840-847 (2003); Kunath et al., *Pharmaceutical Res*, 19: 810-817 (2002); Choi et al., *Bull. Korean Chem. Soc.* 22:46-52 (2001); Bettinger et al., *Bioconjugate Chem.* 10:558-561 (1999); Peterson et al., *Bioconjugate Chem.* 13:845-854 (2002); Erbacher et al., *J. Gene Medicine Preprint* 1:1-18 (1999); Godbey et al., *Proc Natl Acad Sci USA* 96:5177-5181 (1999); Godbey et al., *J Controlled Release* 60:149-160 (1999); Diebold et al., *J Biol Chem* 274:19087-19094 (1999); Thomas and Klibanov, *Proc Natl Acad Sci USA* 99:14640-14645 (2002); and U.S. Pat. No. 6,586,524 to Sagara, each of which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a ligand domain and, e.g., BVR or a fragment or variant thereof as described above. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

When it is desirable to achieve heterologous expression of a desirable protein or polypeptide or inhibitory RNA molecule in a target cell, DNA molecules encoding the desired protein or polypeptide or inhibitory RNA can be delivered into the cell. Basically, this includes providing a nucleic acid molecule encoding the protein or polypeptide or inhibitory RNA, and then introducing the nucleic acid molecule into the cell under conditions effective to express the protein or polypeptide or inhibitory RNA in the cell. Preferably, this is achieved by inserting the nucleic acid molecule into an expression vector before it is introduced into the cell.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chattedee et al., *Science* 258:1485-1488 (1992); Walsh et al., *Proc. Nat'l Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179: 733-738 (1994); Miller et al., *Proc. Nat'l Acad. Sci. USA* 91:10183-10187 (1994); Einerhand et al., *Gene Flier.* 2:336-343 (1995); Luo et al., *Exp. Hematol.* 23:1261-1267 (1995); and Zhou et al., *Gene Thier.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler et al., which is hereby incorporated by reference in its entirety. Lentivirus vectors can also be utilized, including those described in U.S. Pat. No. 6,790,657 to Arya, and U.S. Patent Application Nos. 20040170962 to Kafri et al. and 20040147026 to Arya, each of which is hereby incorporated by reference in its entirety.

Regardless of the type of infective transformation system employed, it should be targeted for delivery of the nucleic acid to a specific cell type. For example, for delivery of the nucleic acid into a cluster of cells, a high titer of the infective transformation system can be injected directly within the site of those cells so as to enhance the likelihood of cell infection. The infected cells will then express the desired product, in this case BVR (or fragments or variants thereof) or antisense BVR RNA, to modify the expression of cell cycle or cell signaling proteins.

Whether the proteins or polypeptides or nucleic acids are administered alone or in combination with pharmaceutically or physiologically acceptable carriers, excipients, or stabilizers, or in solid or liquid form such as, tablets, capsules, powders, solutions, suspensions, or emulsions, they can be administered orally, parenterally, subcutaneously, intravenously, intramuscularly, intraperitoneally, by intranasal instillation, by intracavitary or intravesical instillation, intraocularly, intraarterially, intralesionally, by application to mucous membranes, such as, that of the nose, throat, and bronchial tubes, or by transdermal delivery. For most therapeutic purposes, the proteins or polypeptides or nucleic acids can be administered intravenously.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the proteins or polypeptides or nucleic acids in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Both the biliverdin reductase, or fragment or variant thereof, and the inhibitory RNA can be delivered to the target cells using the above-described methods for delivering such therapeutic products. In delivering the therapeutic products to nerve cells in the brain, consideration should be provided to negotiation of the blood-brain barrier. The blood-brain barrier typically prevents many compounds in the blood stream from entering the tissues and fluids of the brain. Nature provides this mechanism to insure a toxin-free environment for neurologic function. However, it also prevents delivery to the brain of therapeutic compounds.

One approach for negotiating the blood-brain barrier is described in U.S. Pat. No. 5,752,515 to Jolesz et al., which is hereby incorporated by reference in its entirety. Basically, the blood-brain barrier is temporarily "opened" by targeting a selected location in the brain and applying ultrasound to induce, in the central nervous system (CNS) tissues and/or fluids at that location, a change detectable by imaging. A protein or polypeptide or RNA molecule of the present invention can be delivered to the targeted region of the brain while the blood-brain barrier remains "open," allowing targeted neuronal cells to uptake the delivered protein or polypeptide or RNA. At least a portion of the brain in the vicinity of the selected location can be imaged, e.g., via magnetic resonance imaging, to confirm the location of the change. Alternative approaches for negotiating the blood-brain barrier include chimeric peptides and modified liposome structures which contain a PEG moiety (reviewed in Pardridge, *J. Neurochem.* 70:1781-1792 (1998), which is hereby incorporated by reference in its entirety), as well as osmotic opening (i.e., with bradykinin, mannitol, RPM7, etc.) and direct intracerebral infusion (Kroll et al., *Neurosurgery* 42(5):1083-1100 (1998), which is hereby incorporated by reference in its entirety. Any suitable approach for negotiating the blood-brain barrier can be utilized.

EXAMPLES

The following examples are provided to illustrate embodiments of the present invention but are by no means intended to limit its scope.

Materials and Methods

Materials: Human insulin and poly glu/tyr (4:1) were purchased from Sigma-Aldrich (St. Louis, Mo.). Insulin receptor beta (IRK) and insulin receptor substrate-1 (IRS-1) peptide $Y^{608}$ were purchased from Biomol International (Plymouth, Pa.). Monoclonal anti-phosphoserine/anti-phosphothreonine and anti-phosphotyrosine antibodies were obtained from Zymed (San Francisco, Calif.), while [$^{32}$P]-ATP was purchased from Perkin Elmer (Wellesley, Mass.). 2-Deoxy 1-[$^3$H] glucose was purchased from Amersham Pharmacia Biotech (Piscataway, N.J.). Biotrace polivenylidene fluoride (PVDF) transfer membrane was a product of Pall Science corp. (Pensacola, Fla.). Raytide was purchased from Oncogene Science Inc. (Uniondale, N.Y.). Genestein was from Calbiochem (La Jolla, Calif.). Protein A/G plus-agarose was from Santa Cruz Biotechnologies (Santa Cruz, Calif.). Dithiothreitol (DTT) was purchased from Sigma-Aldrich (St. Louis, Mo.). Peptide 1: Lys-Lys-His-Ala-Asp-Asp-Gly-Ala-Met-Pro-Met-Ser$^{312}$-Pro-Gly-Val-Ala (SEQ ID NO: 12); and Peptide 2: Arg-Thr-Glu-Ser$^{307}$-Ile-Thr-Ala-Thr-Ser$^{312}$-Pro-Ala-Ser$^{315}$-Met-Val-Gly-Gly-Lys-Pro (SEQ ID NO: 13) were generated by Synpep (Dublin, Calif.).

Expression vector construction: Expression vector containing full-length human BVR coding sequence were constructed as follows. Initially, for pcDNA3 construct, a clone obtained previously in the laboratory was used to amplify biliverdin reductase cDNA (Maines et al., Eur. J. Biochem. 235:372-81 (1996), which is hereby incorporated by reference in its entirety) using primers: 736BVR (5'-AGAATTC-GATGAATGCAGAGCCCGAGAGGAAGTTTG (SEQ ID NO: 14); and 737BVR (5'-CTGACTCTCGAGTTACTTC-CTTGAACAGCAATATTTCTG (SEQ ID NO: 15)). The resulting fragment was gel purified and digested with restriction endonucleases BamHI and Xho1 followed by ethanol precipitation. The fragments were ligated into expression vector pcDNA3 (Invitrogen, Carlsbad, Calif.), which was digested with the aforementioned restriction enzymes. The ligation mixture was then transformed in to DH5α E. coli chemically competent cells. Selected positive clones for pcDNA3-BVR expression vectors were verified by PCR, restriction analysis, and DNA sequencing. The pGEX 4T-2/ human BVR vector was prepared as described previously (Salim et al., J. Biol. Chem. 276:10929-34 (2001), which is hereby ° incorporated by reference in its entirety). Mutant variants of both pGEX 4T-2 and pcDNA3 constructs were obtained using a QuickChange XL Site-Directed Mutagenesis Kit (Stratagene, La Jolla, Calif.) according to manufacturer's instruction. PAGE purified primers (Integrated DNA Technologies, Coralville, Iowa) were designed as recommended by the supplier and used with the site-directed mutagenesis kit to introduce individual point mutations in the human BVR expression vectors. Unique restriction sites that were not originally found in the human BVR sequence, with the exception of EcoRI, were introduced and facilitated as positive markers for the specific point mutations. In order to obtain double amino acid changes, two consecutive mutagenesis reactions were performed, again according to manufacturer's protocol. Table 1 shows the location of the mutation, the corresponding amino acid change, and unique restriction site introduced in the original human BVR constructs. As verified above, positive mutants were extensively screened via restriction analysis, PCR, and DNA sequencing.

TABLE 1

Location of mutation, corresponding amino acid change, and unique restriction sites introduced in mutant human BVR

| Amino acid | hBVR | Mutation | Restriction marker |
| --- | --- | --- | --- |
| Y72 | VAYIC | VAFIC | NdeI |
| Y83 | EDYIR | EDFIR | HpaII |
| Y98 | VEYPM | VEFPM | EcoRI |
| Y198 | DQYMK | DQFMK | MfeI |
| Y228 | NRYLS | NRFLS | AflII |
| Y291 | QKYCC | QKFCC | ApoI |
| Y198 and Y228 | DQYMK and NRYLS | DQFMK and NRFLS | MfeI, AflII |
| Y198 and Y291 | DQYMK and QKYCC | DQFMK and QKFCC | MfeI, ApoI |
| S21 | AGSVR | AGAVR | HaeII |
| S44 | FVSRR | FVARR | HaeIII |
| S149 | KGSLL | KGALL | EagI |
| S230 | YLSFL | YLAFL | HaeII |
| G17 | GVGRA | GVARA | BssHII |
| T202 | KMTVC | KMAVC | HaeIII |

GST-fusion protein expression in E. coli & purification: The resulting expression of the pGEX 4T-2/hBVR construct and various mutant variants in transformed INV chemically competent cells (Amersham, Piscataway, N.J.) produces human BVR fused to glutathione-S-transferase (GST) protein. Further purification of the GST tagged proteins was performed using a glutathione-Sepharose 4B column (Amersham, Piscataway, N.J.) as previously described (Salim et al., J. Biol. Chem. 276:10929-34 (2001), which is hereby incorporated by reference in its entirety).

siRNA construction and production of pSuper-Retro-siBVR retroviral vector: Motifs for human BVR siRNA (designated siBVR) were selected according to the aa-N19 role by finding the pattern in human BVR cDNA sequences (Maines et al., Eur. J. Biochem. 235:372-81 (1996), which is hereby incorporated by reference in its entirety). The target sequence for the reductase is located at position 96 bp downstream of the start codon (nt96-nt 116). A retroviral based vector pSuper-Retro for siRNA expression was purchased from OligoEngine Co. (Seattle, Wash., USA). siRNA expressing vector pSuper-Retro-siBVR was constructed according to manufacturer's instruction. Briefly, oligos containing the sequence of 21-mer small interference RNA were synthesized using the complimentary oligos:

```
                                        (SEQ ID NO: 16)
5'-GATCCCC (TCC TCA GCG TTC CTG AAC CTG) TTCAAGAGA
(CAG GTT CAG GAA CGC TGA GGA) TTTTTGGAAA (SEQ ID NO: 17)
3'-GGG (AGG AGT CGC AAG GAC TTG GAC) AAGTTCTCT
(GTC CAA GTC CTT GCG ACT CCT) AAAAACCTTTTCGA.
```

The oligos were gel purified and annealed to form double-stranded DNA. To insert the oligos into the pSuper-Retro vector, Bgl II and HindIII were used to digest the vector which was subsequently gel purified. The double-stranded oligos were phosphorylated by T4 kinase. Ligation of the vector and oligos was carried out by incubation of 10 μl of reaction containing 2 μl of vector, 1 μl of oligo, 2 μl of 5× ligation buffer and 1 μl (1U) of T4 ligase for 1 hour at room temperature. 2 μl of the ligation reaction was then used to transform DH5α E. coli. Clones containing the oligo inserts were identified by restriction digest analysis and by DNA sequencing. The resulting vector, pSuper-Retro-siBVR, was transfected into 293A packaging cells (a human embryonic kidney cell line (Invitrogen, Carlsbad, Calif.); and the supernatant containing the expressed siBVR retrovirus was then purified according to supplier's protocol and titrated using NIH3T3 cell line. The concentration of retrovirus expressing siRNA used to infect cells in further experiments was at a multiplicity of infection of 4 pfu/cell.

Cell culture and transfection and infection of 293A: 293A cells were grown in 10 cm-plates with Dulbecco's Modified Eagle Medium (DMEM) (Invitrogen, Carlsbad, Calif.) containing 10% fetal bovine serum and 1% penicillin-G/streptomycin for 24 h or until a confluency of 70% was reached. Cells were subsequently transfected with 4 μg of pcDNA3 mutant BVR $Y^{198}$ using Transfectin Lipid Reagent (Bio-Rad, Hercules, Calif.), according to the manufacturer's procedure and incubated for 48 h at 37° C. In addition, non-transfected cells were infected with pSuper-Retro-siBVR for 24 h in the presence of 4 μg/ml polybrene. Cells were starved in serum-free DMEM 16 h prior to insulin treatment (50 nM).

Measurement of BVR Reductase Activity: 293A cells treated with insulin were lysed in buffer containing a protease inhibitor cocktail and phosphatase inhibitors (10 mM NaF, 1 nM $NaVO_4$). BVR activity was measured at pH 6.7 using NADH as the cofactor as described previously (Huang et al., J. Biol. Chem. 264:7844-9 (1989), which is hereby incorporated by reference in its entirety). The rate of conversion of biliverdin to bilirubin was determined as the increase in absorbance at 450 nm at 25° C. Specific activity is expressed as μmol of bilirubin/min/mg of protein.

BVR autophosphorylation and kinase activity: To detect autophosphorylation of BVR, GST-hBVR of wild type (wt) and mutant variants were incubated in 50 mM HEPES buffer (pH 8.4) in the presence of 30 mM $MnCl_2$ and 1 mM DTT for 2 h at 30° C. The reaction was started with the addition of 10 μM ATP labeled with 10 μCi [γ-$^{32}$P]-ATP and was stopped with the addition of Laemmli sample buffer. Samples were boiled for 3 min and applied to a 8% SDS-PAGE gels, transferred to a PVDF membrane, and then visualized by autoradiography. To measure kinase activity, GST-BVR (5 μg) was incubated in 50 μl kinase buffer containing 50 mM HEPES buffer (pH 8.4), 20 mM $MgCl_2$, 30 mM $MnCl_2$, 1 mM DTT and 10 μM ATP labeled with 10 μCi [γ-$^{32}$P]-ATP in the presence of 5 μg substrates: IRS-1 or Raytide or poly glu/tyr (4:1) for 2 h at 30° C. The reaction was started with the addition of ATP and terminated by adding 120 μl 10% $H_3PO_4$. 100 μl aliquots were directly transferred to P81 Whatman filters which were subsequently washed extensively in 0.75% phosphoric acid at room temperature. Finally, the filters were submerged in acetone for 5 min, dried, and retained counts were measured using a Beckman LS 6500 liquid scintillation counter (Beckman Coulter, Fullerton, Calif.).

BVR phosphoiylation by the insulin receptor tyrosine kinase (IRK): Phosphorylation of BVR by IRK was examined using GST-HBVR fusion protein and the 48 kDa cytoplasmic domain of the β-subunit of IRK. BVR (5 μg) was incubated in 50 μl of IRK kinase buffer containing 50 mM HEPES (pH 8.0), 20 mM $MgCl_2$, 1 mM DTT in the presence of 0.05 μg IRK and 10 μM ATP labeled with 10 μCi [γ-$^{32}$P]-ATP. The reaction was started with the addition of labeled ATP and incubated for 2-4 h. Reactions were terminated by addition of Laemmli sample buffer and boiled for 3 min. Samples were subjected to 8% SDS-PAGE and transferred to PVDF membranes for autoradiography.

Glucose uptake: Glucose uptake was assessed by measuring 2-deoxy 1-[$^3$H] glucose (2DG) absorption as described by (Braiman et al. (Mol. Endocrinol. 13:2002-12 (1999)), which is hereby incorporated by reference), with minor modifications. Briefly, after insulin treatment, cells in 6-wells plates were incubated in 1 ml PBS containing 5 mM glucose and 1 μCi/ml 2DG for 15 min. Solution was aspirated rapidly and wells were washed 3 times with cold PBS. Cells were solubilized by addition of 200 μl 1% (w/v) SDS. Radioactivity was measured and data was normalized to protein concentration. Non-specific uptake was determined in the presence of 200 mM of glucose and was subtracted from the total uptake. Samples were done in triplicate and experiments were repeated three times.

Immunoprecipitation and immunoblotting: 293A Cells were plated in 10 cm plates and transfected with appropriate plasmids. Prior to collection, cells were washed twice with cold PBS and lysed in 300 μl cold modified RIPA buffer containing 50 mM Tris (pH7.4), 75 mM NaCl, 2 mM EDTA, 2 mM EGTA, 10 mM NaF, 1% Nonidet P-40, 0.5% sodium deoxycholate, 0.5% sodium vanadate, 1 mM PMSF, 10 μg/ml aprotinin, 1 mM benzamidine, 10 μg/ml leupeptine, and 10 μg/ml pepstatin. Cells sonicated (2×3 sec each) and centrifuged at 10,000×g for 15 min. Protein concentration was determined by Bradford assay (Bio-Rad, Hercules, Calif.). Polyclonal HBVR antibody (1:50) were generated (McCoubrey et al., Gene 160:235-40 (1995), which is hereby incorporated by reference in its entirety) and added to the lysate and rotated at 4° C. for 3 h. Protein A/G agarose beads were added and the reactions were incubated for another 1 h, followed by centrifugation. The beads were washed twice with RIPA buffer containing protease inhibitors followed by 3 washes with cold PBS. Samples were then subjected to 10% SDS-PAGE and subsequently transferred to PVDF membranes. Blots were probed using anti-phosphotyrosine or anti-hBVR antibodies and visualized by ECL (Perkin-Elmer, Wellesley, Mass.).

Identification of $Y^{198}$ residue by mass spectrometry: Purified BVR protein samples of autophosphorylated BVR, treated and non-treated with IRK, in the presence of 1 mM ATP were separated by SDS-PAGE. The proteins in gel were visualized by Coomassie blue staining (Bio-Rad, Hercules, Calif.). The stained protein bands were excised, subjected to tryptic hydrolysis, and were submitted for mass spectrometry analysis with MALDI-TOF (matrix-assisted laser desorption/ionization time-of-flight) mass spectrometer at two facilities: WEM Biochem, Inc. (Toronto, Canada) (Zhang et al., Eur. J. Biochem. 271:1713-24 (2004), which is hereby incorporated by reference in its entirety) and at the MicroChemical Protein/Peptide Core Facility (University of Rochester, N.Y.) (Polevoda et al., J. Biol. Chem. 278:30686-97 (2003), which is hereby incorporated by reference in its entirety).

Example 1

BVR is a Substrate for the Insulin Receptor Kinase (IRK) and is Phosphorylated In Vitro on Tyrosine Based on the unique protein structure and features of BVR, and its resemblance to certain features of IRK and IRS-1, it was hypothesized that the reductase is a substrate for IRK and a member of the PTK family (FIG. 6). First, whether BVR is a phosphorylation target of IRK was examined. As shown in FIG. 7A, in the presence of IRK, BVR phosphorylation was detected when assessed at 1 h, and gradually increased up to 4 h. The lag period for detection of BVR phosphorylation reflects requirement for IRK activation and autophosphorylation prior to its ability to transfer phosphates to BVR. Findings with anti-phosphotyrosine antibodies shown in FIG. 7B, suggest that BVR is phosphorylated on tyrosine residues and that phosphorylation reflects that of acceptance of phosphate from IRK, and/or autophosphorylation. The role of IRK was suggested by finding that anti-tyrosine antibodies detected BVR in the reaction mixture subsequent to incubation with IRK. The potential for autophosphorylation was implied by observation that purified BVR expressed in $E.\ coli$ displayed basal phospho-tyrosine immunoreactivity; $E.\ coli$ genome does not encode PTKs. The specificity of reactivity was demonstrated by finding that the presence of EDTA, a kinase inhibitor, abolished phosphorylation of BVR by IRK.

Example 2

Tyrosines at Positions $Y^{198}$, $Y^{228}$ and $Y^{291}$ are Targets for IRK-Mediated Phosphorylation Five of the six tyrosine phosphorylation sites in BVR meet the general criteria ascribed to viral PTKs for selection of phosphorylation sites (FIG. 6), which is presence of one or more acidic amino acids N terminal to the tyrosine (Hunter et al., $Annu.\ Rev.\ Biochem.$ 54:897-930 (1985), which is hereby incorporated by reference in its entirety). Based on point mutation analysis, data suggest that IRK exerts selectively for phosphorylation of tyrosine residues. $Y^{198}$ in YMXM motif of BVR was identified as the primary target of IRK. As shown in FIG. 8A, when compared with wtBVR, the point mutation of $Y^{198}$ reduced the xtent of its phosphorylation by nearly 70%. The time course of phosphorylation of $Y^{198}$ mutant BVR is shown in FIG. 8B. As shown, the $Y^{198}$ mutant protein was a less effective substrate for IRK when compared to wtBVR (FIG. 8B vs. FIG. 7B). The finding that $Y^{198}$ detection did not completely abolish phosphorylation of BVR suggested that $Y^{198}$ is not the only tyrosine site that accepts a phosphate group from IRK. To identify tyrosines in BVR that are targets of IRK, BVR preparations each carrying a point mutation of one of the 6 tyrosines were examined for phosphorylation by IRK (FIG. 8C). The results indicated that mutations at $Y^{228}$ and $Y^{291}$ also significantly decreased BVR phosphorylation by IRK (40% and 49% respectively). Point Mutations of $Y^{72}$, $Y^{83}$, and $Y^{98}$ residues did not decrease the extent of BVR phosphorylation by IRK, suggesting that these residues are not targets for IRK-mediated phosphorylation. The assignment of tyrosines as targets of IRK was supported by the finding that little or no phosphorylation was detected with the double mutant $Y^{198}$ plus $Y^{228}$, or $Y^{198}$ plus $Y^{291}$ (FIG. 8D). Further support for phosphorylation of $Y^{198}$ by IRK was sought by mass spectrometry. Purified GST-BVR grown in $E.\ coli$ was subjected to IRK phosphorylation as described supra in the presence of 1 mM ATP. In the control sample, IRK was omitted. The spectrum of both BVR samples, IRK-treated and non-treated had a peak for peptide EDQY$^{198}$MK at 813 Da, but only the IRK treated sample had the phosphorylated peak at 895 Da matching EDQY$^{198}$MK+1P. The analysis is consistent with BVR $Y^{198}$ being the site of phosphorylation by IRK.

As shown in FIG. 1, the $Y^{198}$ in YMXM motif is shared among all of the shown mammalian BVR. The $Y^{228}$ in YLSF motif and the $Y^{291}$ in YCCS motif are both shared among the human, pig, and chimp BVR. These structural consistencies indicate that BVR-IRK interactions are likely conserved among all mammals.

Example 3

Autophosphorylation sites of BVR are Different from the Sites of Phosphorylation Mediated by IRK Further studies were conducted to identify BVR tyrosine residues as targets of autophosphorylation. Autophosphorylation reactions were carried out using the same preparations of BVR tyrosine point mutants. As shown in FIG. 9A, elimination of $Y^{198}$, $Y^{228}$ and $Y^{291}$, which are target sites by IRK phosphorylation (FIG. 8C), did not result in significant changes in autophosphorylation of BVR, while mutations on $Y^{72}$ and $Y^{83}$ markedly decreased autophosphorylation of BVR, suggesting that $Y^{72}$ and $Y^{83}$ are the sites for autophosphorylation of BVR. The phosphotransferase activity of BVR was further explored using two known tyrosine kinase substrates, Raytide and poly-glu/tyr (4:1). Data with Raytide are shown in FIG. 9B, which illustrates that the substrate was effectively phosphorylated by BVR. Poly-glu/tyr was also found to be a substrate for BVR. The observation with $Y^{98}$ does not clarify its role, since unlike the other five tyrosines, it is neither a site of autophosphorylation nor a target for IRK.

Example 4

BVR is Autophosphorylated in the Presence of $Mn^{+2}$ but not $Mg^{+2}$

To further characterize tyrosine kinase activity of BVR, the effect of pH on its kinase activity and specificity for metal ions were examined. wtBVR preparation was incubated at different pH levels: 6.7, 7.5, 8.0, 8.4 and 8.7 in HEPES buffer containing labeled ATP. Autophosphorylation of BVR occurred in basic pH range with pH 8.7, coinciding with the optimal value for its reductase activity with NADPH as the cofactor (Maines et al., $Eur.\ J.\ Biochem.$ 235:372-81 (1996), which is hereby incorporated by reference in its entirety). Accordingly, a mid-point value pH 8.4 was chosen for further studies on BVR autophosphorylation. BVR tyrosine kinase activity exhibited specificity for metal ion, as shown in FIG. 10A, at pH 8.4, autophosphorylation of BVR occurred in the presence of $Mn^{+2}$. When $Mn^{+2}$ was replaced with $Mg^{+2}$, $Ca^{+2}$, or $Zn^{+2}$, autophosphorylation of BVR was almost abolished. $Zn^{+2}$ proved to be inhibitory to BVR autophosphorylation and the presence of $Mn^{+2}$ did not overcome the inhibition, while combined use of $Mn^{+2}+Ca^{+2}$ or $Mn^{+2}+Mg^{+2}$ had no effect on BVR autophosphorylation. The findings with $Zn^{+2}$ are consistent with previous studies that had identified the human BVR as a $Zn^{+2}$ binding protein and had suggested the carboxy terminal segment of the protein as the binding site (Maines et al., $Eur.\ J.\ Biochem.$ 235:372-81 (1996), which is hereby incorporated by reference in its entirety). Because of the extensive interaction between the N terminal ATP binding domain of the protein and the carboxy terminal a helix structure (Whitby et al., $J.\ Mol.\ Biol.$ 319:1199-210 (2002), which is hereby incorporated by reference in its entirety), inhibitory effect of $Zn^{+2}$ could reflect disruption of the interaction and proper fold of the protein.

As shown in FIG. 10A, autophosphorylation of BVR did not occur in the presence of $Mg^{+2}$ at pH 8.0, though IRK specifically phosphorylated BVR under such reaction condition (FIG. 10B). Although most PTKs prefer $Mn^{+2}$ to $Mg^{+2}$, this is not the case with all. Genestein, a PTK inhibitor, significantly inhibited BVR phosphorylation mediated by IRK. Therefore, by using different conditions of pH and metal ions, we were able to minimize BVR autophosphorylation and to detect specific phosphorylation mediated by IRK in the experiments.

Example 5

IRS-1 is Substrate for BVR Kinase Activity

To examine whether serine/threonine kinase activity of BVR is relevant to insulin signaling pathway, BVR kinase activity using IRS-1 as the substrate was studied (FIG. 12). Assay was performed under the conditions that permit its autophosphorylation as defined above. Previous studies had shown that MBP and caseines are substrates for serine phosphotransferase of BVR. First, key serine residues of BVR that are involved in its serine/threonine kinase activity and are contained in known kinase motifs were identified. As shown in FIG. 11A, point mutation of serine residues in BVR sequences associated with kinases resulted in marked decreases in ability of BVR to autophosphorylate. In addition, $T^{202}$ flanking the YMKM motif was also found to be a target of autophosphorylation. In IRS-1 a serine residue flanks the tyrosine binding motif.

That BVR was indeed responsible for phosphorylation of IRS, the reaction was carried out using HO-1 or HO-2 in place of BVR. Both $Mn^{+2}$ and $Mg^{+2}$ were present in the assay system. As shown in FIG. 11B, the incubation of IRS with HO-1 or HO-2 did not significantly effect IRS phosphorylation. Further confirmation of kinase activity of BVR was provided by increased MBP phosphorylated in the presence of BVR. As shown in FIG. 11C, in the presence of increasing amounts of IRS, there was an increase in phosphorylation of BVR by IR up to equimolar ratio of IRS/BVR. The concentration dependence-enhancement of BVR phosphorylation provided additional confirmation for interaction of the two IRK substrates. Final confirmation of BVR kinase activity was provided by BVR carrying point mutation in its ATP binding domain ($GxG^{17}xxG$) on its kinase domain on site $G^{17}$. Kinase assay with this purified protein using a preparation revealed that $G^{17}$ mutation, for the most part, prevented IRS phosphorylation by BVR (FIG. 11D), clearly defining BVR as a kinase for phosphorylation of IRS.

Phosphorylation of IRS on key serines has been shown to inhibit IRS-1 phosphorylation by insulin receptor and several serines had been implicated. The following experiments were conducted to determine whether IRS is a substrate for serine kinase activity of BVR or its tyrosine kinase activity. For these experiments a mutant IRS-1 peptide (#1) and another peptide that has been shown by others to contain serine residues that are targets of phosphorylation were used. The mutant IRS-1 peptide did not contain the tyrosine residue that is present in IRS-1 ($Y^{12}$), which contains three potential phosphorylation sites: $T^{608}$, $Y^{612}$, and $S^{616}$. Also, $T^{608}$ residue was mutated to alanine and only $S^{616}$ was maintained. It was observed that both the mutated and unmutated peptides were phosphorylated to about the same extent (1049±78 cpm and 1081±183 cpm respectively), indicating that $S^{616}$ is the site of BVR phosphorylation. The second IRS-1 peptide (#2) tested contained $S^{307}$, $S^{312}$, and $S^{315}$, the residues that have also been implicated as sites of serine phosphorylation and insulin resistance. The results obtained indicated that this peptide is also a suitable substrate for BVR (1198±230 cpm). These findings indicate that BVR phosphorylates IRS-1 on key serine residues and provide a reasonable basis to believe that IRS serine phosphorylated by BVR contributes to insulin resistance.

Example 6

BVR is an Antagonist to Insulin-Mediated Glucose Uptake by the Cell

Insulin activation of IRK that leads to IRS phosphorylation culminates in increased uptake of glucose. Since the above data revealed that BVR is a substrate of IRK and phosphorylates IRS as a substrate, it was hypothesized that BVR may participate as a regulator in the insulin signaling pathway. The effect of insulin treatment on BVR activation and increased tyrosine phosphorylation in cells were examined to test the hypothesis. As shown in FIGS. 12A-B, treatment with insulin significantly induced BVR reductase activity and tyrosine phosphorylation. When measured 1 h after treatment, a 2-fold increase in activity was detected, which gradually returned to basal level by 6 h after treatment. BVR tyrosine phosphorylation was rapidly increased, and within 8 min after insulin treatment a dramatic increase in phosphorylation was observed (FIG. 12B). The effect of BVR on, and relevance of $Y^{198}$ phosphorylation to insulin-mediated glucose uptake was examined.

To evaluate the effect of BVR on stimulation of glucose uptake by insulin, siRNA for human BVR was used to "knock down" the protein. Cells infected with pSuper-Retro-siBVR vectors or transfected with pcDNA3-$Y^{198}$ mutBVR were obtained and treated with insulin. The rate of uptake of labeled glucose was assessed in treated cells. As shown in FIG. 12C, "knock down" of BVR by siRNA significantly increased insulin-mediated glucose uptake by cells when compared with controls infected with vector alone ($p \leq 0.05$). Glucose uptake by cells transfected with $Y^{198}$ mutBVR was also increased significantly ($p \leq 0.05$), but to a lesser level than that of siRNA. The findings further support the belief that BVR is antagonistic to insulin effect on glucose uptake and its function may be regulated via tyrosine $Y^{198}$ phosphorylation and insulin-mediated activation of BVR.

Discussion of Examples 1-6

The primary and secondary structural features of BVR, plus findings with preliminary experiments that suggested posttranslational modification of BVR on tyrosine residues, made plausible the possibility that the protein is a component of the PTK-regulated signaling cascade and a substrate for the insulin receptor kinase (IRK). The tyrosine phosphorylated IRK substrates serve as docking positions for molecules that contain SH-2 phosphotyrosine binding sites such as phosphatidylinositol (PI) 3-kinase; the primary sequences adjacent to p-tyrosine are required for specific SH-2 domain recognition. The results presented in Examples 1-6 confirm that (i) BVR is a substrate for IR, (ii) BVR is a member of PTK's, and (iii) BVR antagonizes cellular glucose uptake.

The investigation also has identified tyrosine residues that are phosphorylation sites for IRK and those that are autophosphorylated. The N terminal domain tyrosines $Y^{72}$ and $Y^{83}$ are autophosphorylation targets, and the C terminal domain tyrosines $Y^{198}$, $Y^{228}$, $Y^{291}$ are substrates for IRK. Because point mutation of the sixth tyrosine, $Y^{98}$, neither effected phosphorylation of BVR by IRK nor autophosphorylation of BVR, at this time a function cannot be assigned to this residue. The study has also identified IRS-1, which is the primary target of phosphorylation by IRK for insulin-mediated glucose uptake, as a substrate for BVR serine/threonine kinase activity.

Collectively, the findings define BVR as a component of insulin signaling pathway. Furthermore, the identification of the human BVR as a tyrosine kinase characterizes the protein as a member of a small number of kinases, termed dual specificity kinases, which have the ability to autophosphorylate on all three hydroxy amino acids (Menegay et al., *J. Cell Sci.* 113 (Pt 18):3241-53 (2000); Ben-David et al., *EMBO J.* 10:317-25 (1991); Duncan et al., *J. Biol. Chem.* 270:21524-31 (1995); Johnson et al., *J. Biol. Chem.* 266:3402-7 (1991); Lindberg et al., *Trends Biochem. Sci.* 17:114-9 (1992); which are hereby incorporated by reference in their entirety).

Dual specificity kinases are rare groups of kinases that were early on known as LAMMER motif containing proteins (Menegay et al., *J. Cell Sci.* 113 (Pt 18):3241-53 (2000), which is hereby incorporated by reference in its entirety).

Although domains of the dual specificity kinases are indistinguishable from that of serine/threonine kinases, there are certain selective criteria for autophosphorylation of tyrosine residues (Hunter et al., *Annu. Rev. Biochem.* 54:897-930 (1985), which is hereby incorporated by reference in its entirety). In most cases they show preference for $Mn^{+2}$ over $Mg^{+2}$, and much reduced activity with $Ca^{+2}$; this is precisely the observation made with BVR (FIG. 10A). The presently found BVR kinase activity, which was measured under assay conditions that are specific to tyrosine kinases and used *E. coli* as the host for expression of recombinant human BVR, doubtlessly reflects that of the enzyme itself because the *E. coli* genome does not encode PTKs.

In context of kinase activity, there are certain resemblances between BVR and IRK and, in the context of being substrate for IRK, there are similarities between IRS-1 and BVR in residues that flank the key tyrosine phosphorylation sites (FIG. 6). The secondary structure of BVR, unlike IRS proteins, does not have a defined and conserved pleckstrin homology (PH) domain. This domain is the phosphotyrosine binding region of receptor substrates and consists of a sheet of 7 β-strands at one end that interact with a C terminal helix (Blomberg et al., *Trends Biochem. Sci.* 24:441-5 (1999); Dhe-Paganon et al., *Proc. Natl. Acad. Sci. USA* 96:8378-83 (1999); Krupa et al., *J. Mol. Biol.* 339:1025-39 (2004), which are hereby incorporated by reference in their entirety). The phosphotyrosine binding motif of IRS proteins interact with the NPXY motif of IR (Haslam et al., *Nature* 363:309-10 (1993); Pawson, *Nature* 373:573-80 (1995); Sawka-Verhelle et al., *J. Biol. Chem.* 271:5980-3 (1996); Voliovitch et al., *J. Biol. Chem.* 270:18083-7 (1995), which are hereby incorporated by reference in their entirety). The PH domain is divergent at the primary level, on average amounting to about 20%; on the secondary level, however, the structure is conserved. A parallel structure that is present in BVR consists of a 6 strand P-sheet and extensive interaction between the N terminal domain and the C terminal helix (Whitby et al., *J. Mol. Biol.* 319:1199-210 (2002), which is hereby incorporated by reference in its entirety); this would provide an ideal structure for protein: protein interaction. Because a point mutation introduced in the adenine binding domain of BVR (GXGXXG) significantly decreased phosphorylation of IRS by BVR (FIG. 11D), evidently the N terminal domain of BVR must have a key role in the transfer of phosphate to IRS-1, while its C terminal domain functions as a binding site and acceptor of phosphates from IRK.

The present invention has identified two potential SH-2 protein-docking sites in BVR, one of which is $Y^{198}$ in the YMKM motif. Many insulin responses that are associated with cell growth and glucose metabolism are mediated through IRS-1 and IRS-2 complexes (White, *Am. J. Physiol. Endocrinol. Metab.* 283:E413-22 (2002), which is hereby incorporated by reference in its entirety). Interaction of IRS with IRK causes tyrosine phosphorylation of YMXM motifs of IRS proteins (IRS-1-IRS-7) that, in turn, serve as docking sites for SH-2 containing proteins and activation of insulin signaling. The human IRS protein has three copies of YMXM motif, all of which are followed by a serine. BVR has one such motif and it is followed by a threonine, which is target of autophosphorylation by BVR. In case of insulin effect on glucose uptake, docking would involve binding of PI-3 kinase to phosphorylated IRS and activation of Akt (Backer et al., *EMBO J.* 11: 3469-79 (1992), which is hereby incorporated by reference in its entirety). Tyrosine phosphorylated YMXM motif is the preferred binding site for P85 and P55K regulatory subdomains of PI-3 kinase. Based on the defined specificity of Src family for binding site (Myers et al., *Mol. Cell. Biol.* 16:4147-55 (1996); Songyang et al., *Mol. Cell. Biol.* 14:2777-85 (1994); Myers et al., *Trends Biochem. Sci.* 19:289-93 (1994); Pons et al., *Mol. Cell. Biol.* 15:4453-65 (1995), which are hereby incorporated by reference in their entirety), the BVR $Y^{198}$MKM motif predictably would be an ideal site for of PI-3 kinase. PI-3 kinase pathway is a major arm for insulin signaling. PI-3 kinase binding to the IRS and its interaction with downstream substrates leads to modulation of a variety of effector functions in the cell, with glucose transport being one of them.

$Y^{228}$ in YLSF motif meets criteria that provide an optimum binding site for tyrosine phosphorylation of proteins that assemble into a multiprotein/complex that function to recruit and/or facilitate relocation by SH-2 domain containing polypeptides (Songyang et al., *Mol. Cell. Biol.* 14:2777-85 (1994), which is hereby incorporated by reference in its entirety). This includes the SH-2 domain of Src family members, Shc, and SHP-1 tyrosine phosphatases. Presence of more than one SH-2 binding motif in a docking/scaffolding protein is not unusual; for instance, the IRK substrate Gab1 is phosphorylated on multiple tyrosine residues not all of which are associated with YMXM motif (Rocchi et al., *Mol. Endocrinol.* 12:914-23 (1998), which is hereby incorporated by reference in its entirety). In addition, it is worthnoting that the SH2 domains of the p85 regulatory subunit of the kinase interacts with tyrosine-phosphorylated motif receptors, such as toll-like receptors and cytoplasmic 3-phosphoinositide-dependent kinases Serine phosphorylation of the IRS proteins reduces its ability to interact with the receptor and to function as the molecular docking site. Serine phosphorylation sites have been mapped to several residues including $S^{307}$, $S^{312}$, and $S^{616}$ in human IRS-1 (Aguirre et al., *J. Biol. Chem.* 275:9047-54 (2000), De Fea et al., *J. Biol. Chem.* 272:31400-6 (1997); Rui et al., *J. Biol. Chem.* 277:42394-8 (2002); Kanety et al., *J. Biol. Chem.* 270:23780-4 (1995); Feinstein et al., *J. Biol. Chem.* 268:26055-8 (1993); Ravichandran et al., *J. Biol. Chem.* 276:3543-9 (1993); Strack et al., *Diabetologia* 43:443-9 (2000), each of which is hereby incorporated by reference in its entirety). Insulin resistance has been linked to serine phosphorylation of IRS-1. On the basis of finding that BVR phosphorylates synthetic IRS-1 peptides designed not to have tyrosine, but to be otherwise identical to IRS-1 peptide used as substrate for IRK, it is reasonable to believe that IRS-1 is an in vivo substrate for BVR serine/threonine kinase activity.

While most PTKs are associated with cell membranes, there are those PTKs that are not receptor-associated proteins. BVR is a non-receptor tyrosine kinase, and while it is contained mainly in the cytoplasm, activation/hyperphosphorylation of the reductase, for instance by cGMP, leads to its nuclear translocation (Maines et al., *J. Pharmacol. Exp. Ther.* 296:1091-7 (2001), which is hereby incorporated by reference in its entirety). The nuclear localization is relevant to BVR's gene regulatory activity as a member of the BZip family of transcription factors (Ahmad et al., *J. Biol. Chem.* 277:9226-32 (2002), which is hereby incorporated by reference in its entirety) and supports a role for the protein as an anchoring/docking protein. The C terminal domain of the protein downstream from the $Y^{198}$MKM contains a sequence containing a number of positively charged residues: $K^{219}$GPGLKRNR. A motif search identified this sequence as a potential myristoylation site. The sequence shares close similarity to the Src myristoylation signal KDPSQRRN (DeClue et al., *Cancer Res.* 51:712-7 (1991), which is hereby incorporated by reference in its entirety), where the positively charged residues function in binding to membrane phospholipids. The GPG sequence preceding the charged residues permit maximum flexibility for folding of the BVR polypeptide. Previous studies have shown that replacement of positively charged residues in this sequence abrogates nuclear localization of the protein (Maines et al., *J. Pharmacol. Exp. Ther.* 296:1091-1097 (2001), which is hereby incorporated by reference in its entirety).

The results demonstrate that presence of IRS increases phosphorylation of BVR by IRK, and that BVR, independent of IRK, phosphorylates IRS (FIG. 12). When these observations are considered together with the finding of increased insulin-mediated glucose uptake when BVR expression is "knocked down" (FIG. 13), it is reasonable to believe that the negative regulatory phosphorylation of IRS-1 by BVR allows BVR to play a role in the mechanism of insulin resistance. The finding that IRS-1 peptides that contain serine phosphorylation sites, with negative effect on glucose uptake, are target of phosphorylation by BVR is consistent with this assessment. This concept is reinforced by the observation that under assay conditions favorable to IRK activity but not for BVR autophosphorylation, when both substrates BVR and IRS-1 are available to IRK, phosphorylation of BVR is increased. BVR increased phosphorylation in the presence of IRS likely reflects direct interaction of BVR and IRS, as there is precedence for this occurrence. Change in conformation of a kinase initiated by ligand binding can function both in directing proteins to subcellular targets, and to modulate their activity. For instance, ligand binding to ART can activate or inhibit its kinase activity by inducing conformational changes in the kinase that allow its activation/phosphorylation by PDK (Blomberg et al., *Trends Biochem. Sci.* 24:441-5 (1999); Leevers et al., *Curr. Opin. Cell Biol.* 11:219-25 (1999), each of which is hereby incorporated by reference in its entirety). Similarly, the change in conformation of PKC isoforms upon substrate binding or protein/protein interactions unmasks the catalytic domain/phosphorylation site (Newton, *Biochem. J.* 370:361-71 (2003), which is hereby incorporated by reference in its entirety). In the case of BVR, since potentially four tyrosines in the protein can be phosphorylated by IRK, a change in conformation of the protein caused by IRS binding may position a larger number of tyrosine residues for phosphorylation by IRK.

The principle of BVR silencing should be a suitable approach to overcome insulin resistance (and its associated diseases or disorders), while increased expression of BVR could be of value in increasing expression of the genes that function in cell growth and differentiation.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of treating a condition associated with insulin-mediated cellular glucose uptake, said method comprising:

selecting a mammalian subject having a condition associated with insulin-mediated cellular glucose uptake and administering to the subject a C-terminal peptide fragment of biliverdin reductase that comprises an amino acid sequence of YCCS and achieves an increase in insulin-mediated cellular glucose uptake, thereby treating the condition associated with insulin-mediated cellular glucose uptake.

2. The method according to claim 1, wherein the condition is insulin resistance.

3. The method according to claim 1, wherein the condition is selected from the group consisting of type 2 diabetes, hypertension, cardiovascular disease, and obesity.

4. The method according to claim 1, wherein the mammalian subject is a human, a non-human primate, or a rodent.

* * * * *

SEQUENCE LISTING

```
<160> NUMBER OF SEQ ID NOS: 17

<210> SEQ ID NO 1
<211> LENGTH: 296
<212> TYPE: PRT
<213> ORGANISM: Homo sapiens

<400> SEQUENCE: 1

Met Asn Ala Glu Pro Glu Arg Lys Phe Gly Val Val Val Gly Val
1               5                   10                  15

Gly Arg Ala Gly Ser Val Arg Met Arg Asp Leu Arg Asn Pro His Pro
            20                  25                  30

Ser Ser Ala Phe Leu Asn Leu Ile Gly Phe Val Ser Arg Arg Glu Leu
        35                  40                  45

Gly Ser Ile Asp Gly Val Gln Gln Ile Ser Leu Glu Asp Ala Leu Ser
    50                  55                  60

Ser Gln Glu Val Glu Val Ala Tyr Ile Cys Ser Glu Ser Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125
```

```
Leu Met Glu Glu Phe Ala Phe Leu Lys Lys Glu Val Val Gly Lys Asp
    130                 135                 140

Leu Leu Lys Gly Ser Leu Leu Phe Thr Ser Asp Pro Leu Glu Glu Asp
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205

Lys Lys Ser Pro Leu Ser Trp Ile Glu Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 2
<211> LENGTH: 296
<212> TYPE: PRT
<213> ORGANISM: Sus scrofa

<400> SEQUENCE: 2

Met Asn Ala Glu Pro Glu Arg Lys Phe Gly Val Val Val Gly Val Val
1               5                   10                  15

Gly Arg Ala Gly Ser Val Arg Met Arg Asp Leu Arg Asn Pro His Pro
            20                  25                  30

Ser Ser Ala Phe Leu Asn Leu Ile Gly Phe Val Ser Arg Arg Glu Leu
        35                  40                  45

Gly Ser Ile Asp Gly Val Gln Gln Ile Ser Leu Glu Asp Ala Leu Ser
    50                  55                  60

Ser Gln Glu Val Glu Val Ala Tyr Ile Cys Ser Glu Ser Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ala Gly Pro Leu Glu Glu Glu
145                 150                 155                 160

Arg Phe Gly Ser Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205
```

```
Lys Lys Ser Pro Leu Ser Trp Ile Glu Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 3
<211> LENGTH: 295
<212> TYPE: PRT
<213> ORGANISM: Rattus norvegicus

<400> SEQUENCE: 3

Met Asp Ala Glu Pro Lys Arg Lys Phe Gly Val Val Val Gly Val
1               5                   10                  15

Gly Arg Ala Gly Ser Val Arg Leu Arg Asp Leu Lys Asp Pro Arg Ser
                20                  25                  30

Ala Ala Phe Leu Asn Leu Ile Gly Phe Val Ser Arg Arg Glu Leu Gly
            35                  40                  45

Ser Leu Asp Glu Val Arg Gln Ile Ser Leu Glu Asp Ala Leu Arg Ser
        50                  55                  60

Gln Glu Ile Asp Val Ala Tyr Ile Cys Ser Glu Ser Ser Ser His Glu
65                  70                  75                  80

Asp Tyr Ile Arg Gln Phe Leu Gln Ala Gly Lys His Val Leu Val Glu
                85                  90                  95

Tyr Pro Met Thr Leu Ser Phe Ala Ala Ala Gln Glu Leu Trp Glu Leu
            100                 105                 110

Ala Ala Gln Lys Gly Arg Val Leu His Glu Glu His Val Glu Leu Leu
        115                 120                 125

Met Glu Glu Phe Glu Phe Leu Arg Arg Glu Val Leu Gly Lys Glu Leu
130                 135                 140

Leu Lys Gly Ser Leu Arg Phe Thr Ala Ser Pro Leu Glu Glu Glu Arg
145                 150                 155                 160

Phe Gly Phe Pro Ala Phe Ser Gly Ile Ser Arg Leu Thr Trp Leu Val
                165                 170                 175

Ser Leu Phe Gly Glu Leu Ser Leu Ile Ser Ala Thr Leu Glu Glu Arg
            180                 185                 190

Lys Glu Asp Gln Tyr Met Lys Met Thr Val Gln Leu Glu Thr Gln Asn
        195                 200                 205

Lys Gly Leu Leu Ser Trp Ile Glu Glu Lys Gly Pro Gly Leu Lys Arg
    210                 215                 220

Asn Arg Tyr Val Asn Phe Gln Phe Thr Ser Gly Ser Leu Glu Glu Val
225                 230                 235                 240

Pro Ser Val Gly Val Asn Lys Asn Ile Phe Leu Lys Asp Gln Asp Ile
                245                 250                 255

Phe Val Gln Lys Leu Leu Asp Gln Val Ser Ala Glu Asp Leu Ala Ala
            260                 265                 270

Glu Lys Lys Arg Ile Met His Cys Leu Gly Leu Ala Ser Asp Ile Gln
        275                 280                 285
```

```
Lys Leu Cys His Gln Lys Lys
    290             295

<210> SEQ ID NO 4
<211> LENGTH: 295
<212> TYPE: PRT
<213> ORGANISM: Mus musculus

<400> SEQUENCE: 4

Met Ser Thr Glu Pro Lys Arg Lys Phe Gly Val Val Val Gly Val
1               5                   10                  15

Gly Arg Ala Gly Ser Val Arg Ile Arg Asp Ser Lys Asp Pro His Ser
            20                  25                  30

Ser Ala Phe Leu Asn Leu Ile Gly Tyr Val Ser Arg Arg Glu Leu Gly
            35                  40                  45

Ser Leu Asp Asn Val Arg Gln Ile Ser Leu Glu Asp Ala Leu Arg Ser
        50                  55                  60

Gln Glu Val Asp Val Ala Tyr Ile Cys Thr Glu Ser Ser His Glu
65                  70                  75                  80

Asp Tyr Ile Arg Gln Phe Leu Gln Ala Gly Lys His Val Leu Val Glu
                85                  90                  95

Tyr Pro Met Ala Leu Ser Phe Ala Ala Ala Gln Glu Leu Trp Glu Leu
            100                 105                 110

Ala Ala Gln Lys Gly Arg Val Leu His Glu His Ile Glu Leu Leu
            115                 120                 125

Met Glu Glu Phe Glu Phe Leu Lys Arg Glu Val Ala Gly Lys Glu Leu
    130                 135                 140

Leu Lys Gly Ser Leu Arg Phe Thr Ala Ser Pro Leu Glu Glu Lys
145                 150                 155                 160

Phe Gly Phe Pro Ala Phe Ser Gly Ile Ser Arg Leu Thr Trp Leu Val
                165                 170                 175

Ser Leu Phe Gly Glu Leu Ser Leu Ile Ser Ala Thr Met Glu Asn Arg
            180                 185                 190

Lys Glu Asp Gln Tyr Met Lys Met Thr Val Gln Leu Glu Thr Gln Asn
        195                 200                 205

Lys Ser Pro Leu Ser Trp Ile Glu Glu Lys Gly Pro Gly Leu Lys Arg
    210                 215                 220

Asn Arg His Ile Ser Ile His Phe Lys Ser Gly Ser Leu Glu Glu Val
225                 230                 235                 240

Pro Asn Val Gly Val Asn Lys Asn Ile Phe Leu Lys Asp Gln Asp Ile
                245                 250                 255

Phe Ile Gln Lys Leu Leu Gly Val Ser Ala Glu Asp Leu Ala Ala
            260                 265                 270

Glu Lys Lys Arg Ile Leu His Cys Leu Glu Leu Ala Ser Asp Ile Gln
        275                 280                 285

Arg Leu Cys His Arg Lys Gln
    290             295

<210> SEQ ID NO 5
<211> LENGTH: 197
<212> TYPE: PRT
<213> ORGANISM: Pan troglodytes

<400> SEQUENCE: 5

Met Thr Leu Ser Leu Ala Ala Ala Gln Glu Leu Trp Glu Leu Ala Glu
1               5                   10                  15
```

Gln Lys Gly Lys Val Leu His Glu Glu His Val Glu Leu Leu Met Glu
            20                  25                  30

Glu Phe Ala Phe Leu Lys Lys Glu Val Val Gly Lys Asp Leu Leu Lys
        35                  40                  45

Gly Ser Leu Leu Phe Thr Ala Gly Pro Leu Glu Glu Arg Phe Gly
    50                  55                  60

Phe Pro Ala Phe Ser Gly Ile Ser Arg Leu Thr Trp Leu Val Ser Leu
65                  70                  75                  80

Phe Gly Glu Leu Ser Leu Val Ser Ala Thr Leu Glu Glu Arg Lys Glu
                85                  90                  95

Asp Gln Tyr Met Lys Met Thr Val Cys Leu Glu Thr Glu Lys Lys Ser
            100                 105                 110

Pro Leu Ser Trp Ile Glu Glu Lys Gly Pro Gly Leu Lys Arg Asn Arg
        115                 120                 125

Tyr Leu Ser Phe His Phe Lys Ser Gly Ser Leu Glu Asn Val Pro Asn
    130                 135                 140

Val Gly Val Asn Lys Asn Ile Phe Leu Lys Asp Gln Asn Ile Phe Val
145                 150                 155                 160

Gln Lys Leu Leu Gly Gln Phe Ser Glu Lys Glu Leu Ala Ala Glu Lys
                165                 170                 175

Lys Arg Ile Leu His Cys Leu Gly Leu Ala Glu Glu Ile Gln Lys Tyr
            180                 185                 190

Cys Cys Ser Arg Lys
            195

<210> SEQ ID NO 6
<211> LENGTH: 891
<212> TYPE: DNA
<213> ORGANISM: Homo sapiens

<400> SEQUENCE: 6

| | | |
|---|---|---|
| atgaatgcag agcccgagag gaagtttggc gtggtggtgg ttggtgttgg ccgagccggc | 60 |
| tccgtgcgga tgagggactt gcggaatcca cacccttcct cagcgttcct gaacctgatt | 120 |
| ggcttcgtgt cgagaaggga gctcgggagc attgatggag tccagcagat ttctttggag | 180 |
| gatgctcttt ccagccaaga ggtggaggtc gcctatatct gcagtgagag ctccagccat | 240 |
| gaggactaca tcaggcagtt ccttaatgct ggcaagcacg tccttgtgga ataccccatg | 300 |
| acactgtcat tggcggccgc tcaggaactg tgggagctgg ctgagcagaa aggaaaagtc | 360 |
| ttgcacgagg agcatgttga actcttgatg gaggaattcg ctttcctgaa aaaagaagtg | 420 |
| gtggggaaag acctgctgaa agggtcgctc ctcttcacat ctgacccgtt ggaagaagac | 480 |
| cggtttggct tccctgcatt cagcggcatc tctcgactga cctggctggt ctccctcttt | 540 |
| ggggagcttt ctcttgtgtc tgccactttg gaagagcgaa aggaagatca gtatatgaaa | 600 |
| atgacagtgt gtctggagac agaagaaaa agtccactgt catggattga agaaaaagga | 660 |
| cctggtctaa aacgaaacag atatttaagc ttccatttca gtctgggtc cttggagaat | 720 |
| gtgccaaatg taggagtgaa taagaacata tttctgaaag atcaaaatat atttgtccag | 780 |
| aaactcttgg gccagttctc tgagaaggaa ctggctgctg aaaagaaacg catcctgcac | 840 |
| tgcctggggc ttgcagaaga aatccagaaa tattgctgtt caaggaagta a | 891 |

<210> SEQ ID NO 7
<211> LENGTH: 888
<212> TYPE: DNA
<213> ORGANISM: Rattus norvegicus

<400> SEQUENCE: 7

```
atggatgccg agccaaagag gaaatttgga gtggtagtgg ttggtgttgg cagagctggc        60
tcggtgaggc tgagggactt gaaggatcca cgctctgcag cattcctgaa cctgattgga       120
tttgtgtcca gacgagagct tgggagcctt gatgaagtac ggcagatttc tttggaagat       180
gctctccgaa gccaagagat tgatgtcgcc tatatttgca gtgagagttc cagccatgaa       240
gactatatac ggcagtttct gcaggctggc aagcatgtcc tcgtggaata ccccatgaca       300
ctgtcatttg cggcggccca ggagctgtgg gagctggccg cacagaaagg gagagtcctg       360
catgaggagc acgtggaact cttgatggag gaattcgaat tcctgagaag agaagtgttg       420
gggaaagagc tactgaaagg gtctcttcgc ttcacagcta gcccactgga agaagagaga       480
tttggcttcc ctgcgttcag cggcatttct cgcctgacct ggctggtctc cctcttcggg       540
gagctttctc ttatttctgc caccttggaa gagcgaaaag aggatcagta tatgaaaatg       600
accgtgcagc tggagaccca gaacaagggt ctgctgtcat ggattgaaga aaagggcct        660
ggcttaaaaa gaaacagata tgtaaacttc cagttcactt ctgggtccct ggaggaagtg       720
ccaagtgtag gggtcaataa gaacattttc ctgaaagatc aggatatatt tgttcagaag       780
ctcttagacc aggtctctgc agaggacctg gctgctgaga agaagcgcat catgcattgc       840
ctggggctgg ccagcgacat ccagaagctt tgccaccaga agaagtga                    888
```

<210> SEQ ID NO 8
<211> LENGTH: 891
<212> TYPE: DNA
<213> ORGANISM: Sus scrofa

<400> SEQUENCE: 8

```
atgaatgcag agcccgagag gaagtttggc gtggtggtgg ttggtgttgg ccgagccggc        60
tccgtgcgga tgagggactt gcggaatcca caccttcct cagcgttcct gaacctgatt        120
ggcttcgtgt cgagaaggga gctcgggagc attgatgagt ccagcagat ttctttggag        180
gatgctcttt ccagccaaga ggtggaggtc gcctatatct gcagtgagag ctccagccat       240
gaggactaca tcaggcagtt ccttaatgct ggcaagcacg tccttgtgga ataccccatg       300
acactgtcat ggcggccgc tcaggaactg tgggagctgg ctgagcagaa aggaaaagtc       360
ttgcacgagg agcatgttga actcttgatg gaggaattcg ctttcctgaa aaagaagtg       420
gtggggaaag acctgctgaa agggtcgctc ctcttcacag ctggcccgtt ggaagaagag       480
cggtttggct cccctgcatt cagcggcatc tctcgcctga cctggctggt ctccctcttt       540
ggggagcttt ctcttgtgtc tgccactttg gaagagcgaa aggaagatca gtatatgaaa       600
atgacagtgt gtctggagac agagaagaaa agtccactgt catggattga agaaaaagga       660
cctggtctaa aacgaaacag atatttaagc ttccatttca gtctgggtc cttggagaat        720
gtgccaaacg taggagtgaa taagaacata tttctgaaag atcaaaatat atttgtccag       780
aaactcttgg ccagttctc tgagaaggaa ctggctgctg aaaagaaacg catcctgcac       840
tgcctggggc ttgcagaaga aatccagaaa tattgctgtt caaggaagta a                891
```

<210> SEQ ID NO 9
<211> LENGTH: 594
<212> TYPE: DNA
<213> ORGANISM: Pan troglodytes

<400> SEQUENCE: 9

```
ttacttcctt gaacagcaat atttctggat ttcttctgca gccccaggc agtgcaggat         60
```

```
gcgtttcttt tcagcagcca gttccttctc agagaactgg cccaagagtt tctggacaaa    120
tatattttga tctttcagaa atatgttctt attcactcct acatttggca cattctccaa    180
ggacccagac ttgaaatgga aacttaaata tctgtttcgt tttagaccag gtccttttc    240 ttcaatccat gacagtggac ttttcttctc tgtctccaga cacactgtca ttttcatata    300
ctgatcttcc tttcgctctt ccaaagtggc agacacaaga gaaagctccc caaagaggga    360
gaccagccag gtcaggcgag agatgccgct gaatgcaggg aagccaaacc gctcttcttc    420
caacgggcca gctgtgaaga ggagcgaccc tttcagcagg tctttcccca ccacttcttt    480
tttcaggaaa gcgaattcct ccatcaagag ttcaacatgc tcctcgtgca agacttttcc    540
tttctgctca gccagctccc acagttcctg agcggccgcc aatgacagtg tcat         594
```

<210> SEQ ID NO 10
<211> LENGTH: 21
<212> TYPE: RNA
<213> ORGANISM: Artificial
<220> FEATURE:
<223> OTHER INFORMATION: siRNA for Homo sapiens BVR

<400> SEQUENCE: 10
uccucagcgu uccugaaccu g                                              21

<210> SEQ ID NO 11
<211> LENGTH: 21
<212> TYPE: RNA
<213> ORGANISM: Artificial
<220> FEATURE:
<223> OTHER INFORMATION: siRNA for Homo sapiens BVR

<400> SEQUENCE: 11
cagguucagg aacgcugagg a                                              21

<210> SEQ ID NO 12
<211> LENGTH: 16
<212> TYPE: PRT
<213> ORGANISM: Artificial
<220> FEATURE:
<223> OTHER INFORMATION: mutant peptide fragment of Homo sapiens Insulin
      Receptor Substrate (Peptide 1)

<400> SEQUENCE: 12

Lys Lys His Ala Asp Asp Gly Ala Met Pro Met Ser Pro Gly Val Ala
1               5                   10                  15

<210> SEQ ID NO 13
<211> LENGTH: 18
<212> TYPE: PRT
<213> ORGANISM: Artificial
<220> FEATURE:
<223> OTHER INFORMATION: peptide fragment of Homo sapiens Insulin
      Receptor Substrate (Peptide 2)

<400> SEQUENCE: 13

Arg Thr Glu Ser Ile Thr Ala Thr Ser Pro Ala Ser Met Val Gly Gly
1               5                   10                  15

Lys Pro

<210> SEQ ID NO 14
<211> LENGTH: 36
<212> TYPE: DNA
<213> ORGANISM: Artificial
<220> FEATURE:
<223> OTHER INFORMATION: primer for Homo sapiens BVR (Primer 736BVR)

-continued

```
<400> SEQUENCE: 14
agaattcgat gaatgcagag cccgagagga agtttg                              36

<210> SEQ ID NO 15
<211> LENGTH: 39
<212> TYPE: DNA
<213> ORGANISM: Artificial
<220> FEATURE:
<223> OTHER INFORMATION: primer for Homo sapiens BVR (Primer 737BVR)

<400> SEQUENCE: 15
ctgactctcg agttacttcc ttgaacagca atatttctg                           39

<210> SEQ ID NO 16
<211> LENGTH: 68
<212> TYPE: DNA
<213> ORGANISM: Artificial
<220> FEATURE:
<223> OTHER INFORMATION: oligonucleotide encoding siRNA for Homo sapiens
      BVR (sense strand)

<400> SEQUENCE: 16
gatcccctcc tcagcgttcc tgaacctgtt caagagacag gttcaggaac gctgaggatt    60
tttggaaa                                                             68

<210> SEQ ID NO 17
<211> LENGTH: 68
<212> TYPE: DNA
<213> ORGANISM: Artificial
<220> FEATURE:
<223> OTHER INFORMATION: oligonucleotide encoding siRNA for Homo sapiens
      BVR (antisense strand)

<400> SEQUENCE: 17
agcttttcca aaaatcctca gcgttcctga acctgtctct tgaacaggtt caggaacgct    60
gaggaggg                                                             68
```